US010195466B2

(12) United States Patent
Suh et al.

(10) Patent No.: US 10,195,466 B2
(45) Date of Patent: Feb. 5, 2019

(54) METHOD FOR TREATING SKIN CANCER USING RADIATION THERAPY

(71) Applicant: HACKENSACK UNIVERSITY MEDICAL CENTER, Hackensack, NJ (US)

(72) Inventors: K. Stephen Suh, Hackensack, NJ (US); Sreeja Sarojini, Ridgewood, NJ (US); Mehmet Tuna, Hackensack, NJ (US); Joseph Barbiere, Hackensack, NJ (US); Alois M. Ndlovu, Hackensack, NJ (US); Andrew L. Pecora, Hackensack, NJ (US); Anthony Ingenito, Hackensack, NJ (US)

(73) Assignee: HACKENSACK UNIVERSITY MEDICAL CENTER, Hackensack, NJ (US)

( * ) Notice: Subject to any disclaimer, the term of this patent is extended or adjusted under 35 U.S.C. 154(b) by 373 days.

(21) Appl. No.: 14/591,299

(22) Filed: Jan. 7, 2015

(65) Prior Publication Data
US 2015/0352378 A1 Dec. 10, 2015

Related U.S. Application Data

(60) Provisional application No. 61/923,994, filed on Jan. 6, 2014.

(51) Int. Cl.
A61N 5/10 (2006.01)
A61K 31/353 (2006.01)
(Continued)

(52) U.S. Cl.
CPC .......... *A61N 5/1077* (2013.01); *A61K 31/337* (2013.01); *A61K 31/353* (2013.01);
(Continued)

(58) Field of Classification Search
CPC ................ A61N 5/1031; A61N 5/1077; A61N 2005/1098; A61K 31/353; A61K 31/337; A61K 31/365
See application file for complete search history.

(56) References Cited

U.S. PATENT DOCUMENTS 7,963,902 B2 * 6/2011 Blankenbecler ......... A61N 5/10 600/1
8,173,983 B1 * 5/2012 Sahadevan ........... A61N 5/1084 250/341.7

(Continued)

OTHER PUBLICATIONS

Hezewijk M.V., et al., "Efficacy of a hypofractionated schedule in electron beam radiotherapy for epithelial skin cancer: Analysis of 434 cases", Radiotherapy and Oncology, 2010, vol. 95, pp. 245-249.

(Continued)

Primary Examiner — Christine H Matthews
Assistant Examiner — Joshua D Lannu
(74) Attorney, Agent, or Firm — McCarter & English, LLP; Beverly W. Lubit

(57) ABSTRACT

The described invention provides methods for irradiating skin cancer cells, such as melanoma cells, at a high radiation rate (e.g., of 2,400 mu/min) and a modest total dose (e.g., of 0.5 Gy) to treat skin cancer or induce apoptosis in skin cancer cells. The radiation may be administered in a plurality of treatments and used in conjunction with chemotherapy.

22 Claims, 21 Drawing Sheets

(51) Int. Cl.
  *A61K 31/337* (2006.01)
  *A61K 31/365* (2006.01)
(52) U.S. Cl.
  CPC .......... *A61K 31/365* (2013.01); *A61N 5/1031* (2013.01); *A61N 2005/1098* (2013.01)

(56) References Cited

U.S. PATENT DOCUMENTS

| | | | | |
|---|---|---|---|---|
| 2003/0060505 | A1* | 3/2003 | Reddy | A61K 31/10 514/461 |
| 2009/0082295 | A1* | 3/2009 | Jungnelius | A61K 31/337 514/44 R |
| 2009/0324682 | A1* | 12/2009 | Popowski | A61K 9/0024 424/426 |

OTHER PUBLICATIONS

Locke J. et al., "Radiotherapy for epithelial skin cancer", Int. J. Radiation Oncology Biol. Phys, 2001, vol. 51, pp. 748-755.
Lohse I., et al., "Effect of high dose per pulse flattening filter-free beams on cancer cell survival", Radiotherapy and Oncology, 2011, vol. 101, pp. 226-232.
Parida D.K., et al., "Total skin electron irradiation therapy in mycosis fungoides using high-dose rate mode: A preliminary experience", International Journal of Dermatology, 2005, vol. 44, pp. 828-830.
Varian: "The TrueBeam System", 2013, pp. 1-16, retrieved from the internet: URL:http://www.variantruebeam.com/pdf/TrueBeam_Brochure.pdf.
Chang Z., et al., "Commissioning and dosimetric characteristics of TrueBeam system: Composite data of three TrueBeam machines", Med. Phys., 2012, vol. 39, pp. 6981-7018.
Adams E.J., et al., "Clinical implementation of dynamic and step-and-shoot IMRT to treat prostate cancer with high risk of pelvic lymph node involvement", Radiotherapy and Oncolocy, 2004, vol. 70, pp. 1-10.
Balk S.J., et al., "Teens and indoor tanning: A cancer prevention opportunity for pediatrician", Pediatrics, 2013, vol. 131, pp. 772-785.
Balch C.M., et al., "Final version of the american joint committee on cancer staging system for cutaneous melanoma", Journal of Clinial Oncology, vol. 19, pp. 3635-3648.
Broderick M, et al., "Direct aperture optimization as a means of reducing the complexity of intensity modulated radiation therapy plans" Radiation Oncology, 2009, vol. 4, pp. 1-7.
Bucci M.K., et al., "Advances in radiation therapy: Conventional to 3D, to IMRT, to 4D, and beyond", CA Cancer J Clin, 2005, vol. 55, pp. 117-134.
Chalmers A.H., et al., "Resistance of human melanoma cells to ultraviolet radiation", Cancer Research, 1976, vol. 36, pp. 1930-1934.
Colombino, M., et al., "BRAF/NRAS mutation frequencies among primary tumors and metastases in patients with melanoma", Journal of Clinical Oncology, 2012, vol. 30, pp. 2522-2529.
Combs S.E, et al., "Local high-dose radiotherapy and sparing of normal tissue using intensity-modulated radiotherapy (IMRT) for mucosal melanoma of the nasal cavity and paranasal sinuses", Strahlenter Onkol, 2007, vol. 2, pp. 63-68.
Ezzell G.A., et al., "Guidance document on delivery, treatment planning, and clinical implementation of IMRT: Report of the IMRT subcommitte of the AAPM radiation therapy committe", 2003, vol. 30, pp. 2089-2115.
Garbe C. et al., "Diagnosis and treatment of melanoma: European consensus-based interdisciplinary guideline", European Journal of Cancer, 2010, vol. 46, pp. 270-283.
Gierga D.P. et al., "Quantification of respiration-induced abdominal tumor motion and its impact on IMRT dose distributions", Int. J. Radiation Oncology Biol. Phys., 2004, vol. 58, pp. 1584-1595.

Kestin L.L., et al., "Intensity modulation to improve does uniformity with tangenial breast radiotherapy: Initial clinical experience", Int. J. Radiation Oncology Biol. Phys., 2000, vol. 48, pp. 1559-1568.
Khan M.K., et al., "Future of radiation therapy for malignant melanoma in an era of newer, more effective biological agents", Onco Targets and Therapy, 2011, vol. 4, pp. 137-148.
Kirkwood J.M., et al., High-Dose interferon alfa-2b significantly prolongs relapse-free and overall survival compared with GM2-KLH/QS-21 vaccine in patients with resected stage IIB-III melanoma: Results of intergroup trail E1694/S9512/C509801, Journal of Clinical Oncology, 2001, vol. 19, pp. 2370-2380.
Levine S.M., et al., "Surgical treatment of malignant melanoma practical guidelines", Dermatol Clin, 2012, vol. 30, pp. 487-501.
Li J., et al., "Improvements in dose accuracy delivered with static-MLC IMRT on an integrated linear accelerator control system", Med. Phys., 2012, vol. 39, pp. 2456-2462.
Little E.G., et al., "Update on the current state of melanoma incidence", Dermatol Clin, 2012, vol. 30, pp. 355-361.
McCubrey J.A., et al., "Roles of the RAF/MEK/ERK and PI3K/PTEN/AKT pathways in malignant transformation and drug resistance", Advan. Enzyme Regul., 2006, vol. 46, pp. 249-279.
Rafehi H., et al., "Clonogenic assay: Adherent cells", Journal of Visualized Experiments, 2011, vol. 49, pp. 1-3.
Rogers H.W., et al., "Incidence estimate of nonmelanoma skin cancer in the United States", Arch Dermato, 2010, vol. 46, pp. 283-287.
Scorsetti M., et al., "Feasibility and early clinical assessment of flattening filter free (FFF) based stereotactic body radiotherapy (SBRT) treatments", Radiation Oncology, 2011, vol. 113, pp. 1-8.
Shepard D.M., "Optimizing the delivery of radiation therapy to cancer patients", SIAM Review, 1999, vol. 41, pp. 721-744, Society for Industrial and Applied Mathematics.
Siegel R., et al., "Cancer Statistics, 2012", CA: A Cancer Journal for Clinicians, 2012, vol. 62, pp. 10-29.
Stevens G., et al., "Dispelling the myths surrounding radiotherapy for treatment of cutaneous melanoma", Lancet Oncol., 2006, vol. 7, pp. 575-583.
Wu XC, et al., Racial and ethnic variations in incidence and survival of cutaneous melanoma in the United States, 1999-2006, 2011, J Am Acad Dermatol, vol. 65, pp. 1-13.
Xu X.G., et al., "A review of dosimetry studies on external-beam radiation treatment with respect to second cancer induction", Phys Med Biol., 2008, vol. 53, pp. 193-241.
Zelefsky M.J., et al., "Clinical experience with intensity modulated radiation therapy (IMRT) in prostate cancer", Radiotherapy and Oncology, 2000, vol. 55, pp. 241-249.
Forschner A., et al., "The role of radiotherapy in the overall treatment of melanoma", Clinics in Dermatology, 2013, vol. 31, pp. 282-289.
Calabro A., et al., "Patterns of relapse in 1001 consecutive patients with melanoma nodal metastases", Arch Surg, 1989, vol. 124, pp. 1051-1055.
Hallemeier C.L, et al., "Adjuvant hypofractionated intensity modulated radiation therapy after resection of regional lymph node metastases in patients with cutaneous malignant melanoma of the head and neck", Practical Radiation Oncology, 2013, vol. 3, pp. 71-77.
Byers R.M.,"The role of modified neck dissection in the treatment of cutaneous melanoma of the head and neck", 1986, Arch Surg, vol. 121, pp. 1338-1341.
Stevens G., et al., "Radiation therapy in the management of cutaneous melanoma", Surg Oncol Clin N Am, 2006, vol. 15, pp. 353-371, Elsevier Saunders.
Palta J.R., et al., "Quality assurance of intensity-modulated radiation therapy", Int. J. Radiation Oncology Biol. Phys., 2008, Int. J. Radiation Oncology Biol. Phys., 2008, vol. 71, pp. S108-S112.
Calipel, A. et al, Mutation of B-Raf in Human Choroidal Melanoma Cells Mediates Cell Proliferation and Transformation through the MEK/ERK Pathway, The Journal of Bilogical Chemistry, vol. 278, No. 43, Issue of Oct. 24, pp. 42409-42418, 2003.

(56) References Cited

OTHER PUBLICATIONS

Gembarska, A. et al., 'MDM4 is a key therapeutic target in cutaneous melanoma', Nature Medicine, 2012, vol. 18, No. 8, pp. 1239-1249.

Kalantzis, G. et al., 'Fidelity of dose delivery at high dose rate of volumetric modulated arc therapy in a truebeam linac with flattening filter free beams', Journal of Medical Physics, 2012, vol. 37, No. 4, pp. 193-199.

Loberg, RD, et al., Enhanced Glycogen Synthase Kinase-3 Activity Mediates Hypoxia-induced Apoptosis of Vascular Smooth Muscle Cells and is Prevented by Glucose Transport and Metabolism*, J. Biol. Chem. 277 (44): 41667-673 (2002).

Longo, Caterina, et al., "Superficial spreading melanoma." Reflectance Confocal Microscopy for Skin Diseases, Springer Berlin Heidelberg 2012. 151-178.

Pinkoski, MJ, Green, DR, "Fas ligand, death gene," Cell Death Differ. 6(12): 1174-81 (1999).

Prendergast, B.M. et al., 'Stereotactic body radiation therapy (SBRT) for lung malignancies: preliminary toxicity results using a flattening filter-free linear accelerator operating at 2400 monitor units per minute', Radiation Oncology, 2013, vol. 8, p. 273.

Purdy, James A "From new frontiers to new standards of practice: advances in radiotherapy planning and delivery" (2007): 18-39.

Ramsay, E.E. et al., 'Mitochondrial Metabolism Inhibitors for Cancer Therapy', Pharmaceutical Research, 2011, vol. 28, No. 11, pp. 2731-2744.

Rofstad, E.K., 'Radiation Sensitivity in Vitro of Primary Tumors and Metastatic Lesions of Malignant Melanoma', Cancer Research, 1992, vol. 52, pp. 4453-4457.

W. Kolch, Meaningful relationships: the regulation of the Ras/Raf/MEK/ERK pathway by protein interactions, Biochem J. 2000.

Wolff, Dirk, et al. "Volumetric modulated arc therapy (VMAT) vs. serial tomotherapy, step-and-shoot IMRT and 3D-confonnal RT for treatment of prostate cancer." Radiotherapy and Oncology 93.2 (2009): 226-233.

* cited by examiner

FIG. 2B
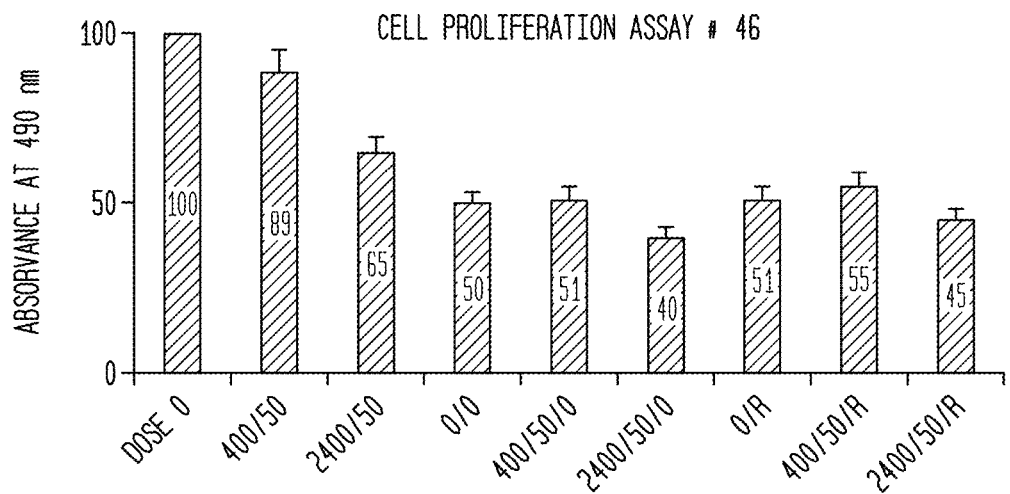
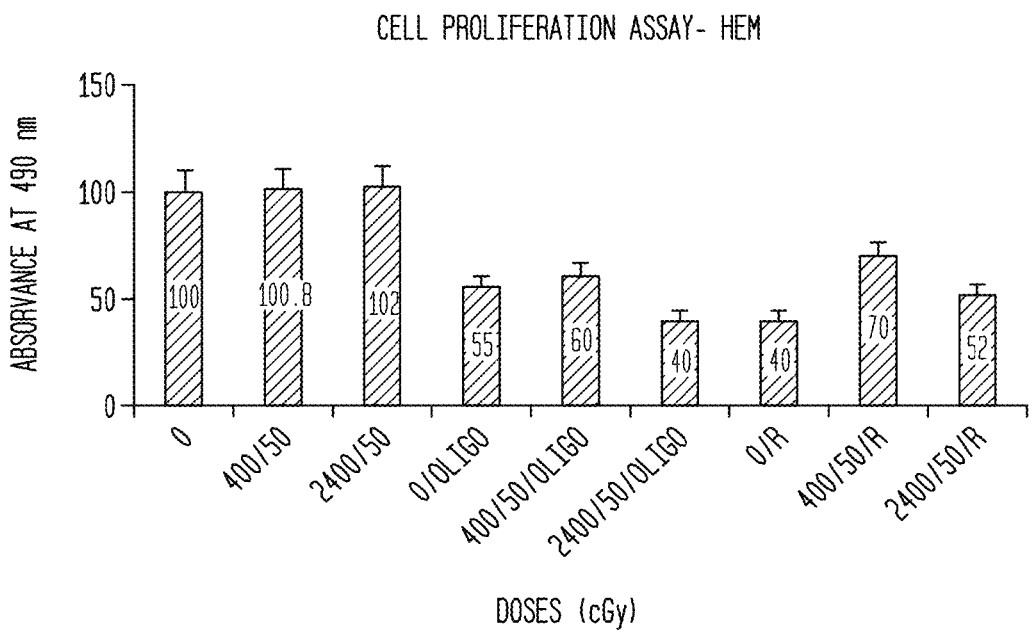

MIGRATION ASSAY

FIG. 5B

RT-PCR RESULTS [MELANOMA CELLS AND HEM]

| GENES | FUNCTIONS | MELANOMA CELLS [46] | | | | HEM | | | |
|---|---|---|---|---|---|---|---|---|---|
| | | 400 | | 2400 | | 400 | | 2400 | |
| CASPASE 3 | APOPTOSIS | 12 | ⇒ | 3 | ⇒ | 1 | ⇐ | 2 | ⇐ |
| CASPASE 9 | APOPTOSIS | 10 | ⇒ | 2 | ⇒ | 2 | ⇐ | 1 | ⇐ |
| MCL1 | ANTI-APOPTOSIS | 3 | ⇒ | 1 | ⇐ | 2 | ⇐ | 5 | ⇐ |
| BCL2 | ANTI-APOPTOSIS | 4 | ⇐ | 1 | ⇐ | 2 | ⇐ | 10 | ⇐ |
| NDUFS | RESPIRATION | 2 | ⇐ | 20 | ⇐ | 2 | ⇐ | 10 | ⇐ |
| UCRC | RESPIRATION | 2 | ⇐ | 4 | ⇐ | 2 | ⇐ | 15 | ⇐ |
| ATF6 | RESPIRATION | 2 | ⇒ | 8 | ⇐ | 2 | ⇐ | 3 | ⇐ |
| SDHC | RESPIRATION | 8 | ⇒ | 16 | ⇒ | 4 | ⇐ | 15 | ⇐ |
| NOXA | ER- STRESS | 3 | ⇒ | 1 | ⇐ | 10 | ⇐ | 120 | ⇐ |
| PERK | ER- STRESS | 8 | ⇐ | 3 | ⇐ | 1 | ⇐ | 2 | ⇐ |
| BRAF | ONCOGENE | 60 | ⇐ | 70 | NORMAL | | NORMAL | | |
| HEM | HOUSEKEEPING | NA | | NA | | NA | | NA | |
| GAPDH | HOUSEKEEPING | NA | | NA | | NA | | NA | |

FIG. 11A

TALE 1. AVERAGE FOLD CHANGES OF SPECIFIC TARGETED GENES
IN HEM AND MELANOMA CELLS AT 50 cGy
(400cGy/min VS. 2400cGy/min)

| GENES | FUNCTION | HEM AVERAGE FOLD CHANGE AT 50cGy | | MELANOMA AVERAGE FOLD CHANGE AT 50cGy | |
|---|---|---|---|---|---|
| | | 400cGY/min | 2400cGY/min | 400cGY/min | 2400cGY/min |
| GAPDH | HOUSE KEEPING GENE FOR NORMALIZING RNA EXPRESSION IN PCR | +1 | +1 | +1 | +1 |
| PTEN | INVOLVED IN NUCLEUS-INIDUCED APOPTOSIS | +6 | +4 | +4 | +20 |
| CASPASE 9 | EXECUTION OF MITOCHONDRION-INDUCED APOPTOSIS FOLLOWING CASPASE 3 | +6 | +8 | +8 | +26 |
| UCRC | EXPRESSLY LINKED TO MITOCHONDRIAL RESPIRATION CHAIN COMPLEX | +4 | +12 | +3 | +6 |
| ATPAF2 | RESPONSIBLE FOR ASSEMBLY FACTOR OF COMPONENTS IN MITOCHONDRIAL ATP SYNTHASE | +2 | +3 | +2 | +8 |
| CYCLIN D1 | CELL CYCLE REGULATOR GENE | +2 | +3 | -2 | -3 |
| MSH-2 | DNA MISMATCH AND DAMAGE RECONGNITION GENE | +3 | +8 | -1 | +1 |

FIG. 11B

THE AVERAGE FOLD CHANGES IN SELECTED GENE EXPRESSION LEVELS

| GENES | FUNCTION | MELANOMA CELLS (# 46) | | HEM | |
|---|---|---|---|---|---|
| | | AVERAGE FOLD CHANGE AT 400/50 cGy | AVERAGE FOLD CHANGE AT 2400/50 cGy | AVERAGE FOLD CHANGE AT 400/50 cGy | AVERAGE FOLD CHANGE AT 2400/50 cGy |
| BCL2 | ANTI-APOPTOSIS, ENCODES AN INTEGRAL OUTER MITOCHONDRIAL MEMBRANE PROTEIN THAT BLOCKS THE APOPTOTIC DEATH | -4 | -1 | 8 | 10 |
| MCL1 | ANTI-APOPTOSIS (ISOFORM 2 AND 3) | 2 | 4 | 4 | 5 |
| CASPASE 3 | INVOLVED IN THE ACTIVATION CASCADE OF CASPASES RESPONSIBLE FOR APOPTOSIS EXECUTION | -3 | -4 | 2 | 3 |
| CASPASE 9 | APOPTOSIS GENE, ACTIVATED BY CASP 3 | 8 | 25 | 5 | 8 |
| NDUFS2 | SUBUNIT OF THE MITOCHONDRIAL MEMBRANE RESPIRATORY CHAIN NADH DEHYDROGENASE (COMPLEX I) | 3 | 6 | 4 | 12 |
| UCRC | MITOCHONDRIAL RESPIRATORY CHAIN | -2 | -4 | 18 | 10 |
| ATF6 | SEGMENT OF THE RESPIRATORY CHAIN OF THE INNER MITOCHONDRIAL MEMBRANE | 2 | 8 | 2 | 3 |
| SDHC | RESPIRATION | 4 | 3 | 20 | 22 |
| NOXA | ER-STRESS GENE, REPRESENT A MEDIATOR OF p53-DEPENDENT APOPTOSIS | -3 | -1 | 4 | 6 |
| PERK | ER-STRESS | -2 | -7 | 3 | 4 |
| BRAF | PROTO-ONCOGENE B-Ra | 10 | 12 | 1 | 1 |
| BAX | APOPTOSIS (REGULATED BY p53 GENE) | -5 | -9 | 2 | 3 |
| COX | RESPIRATION, CYTOCHROME C OXIDASE (COX) IS THE TERMINAL ENZYME OF THE MITOCHONDRIAL RESPIRATORY CHAIN | 15 | 10 | 2 | 3 |
| PUMA | BH3-ONLY PRO-APOPTOTIC SUBCLASS, INDUCES CASPASE ACTIVATION* | 25 | 38 | 5 | 8 |
| ATPAF2 | ENCODES AN ASSEMBLY FACTOR FOR THE F(1) COMPONENT OF THE MITOCHONDRIAL ATP SYNTHASE | 5 | 10 | 8 | 12 |
| B2M | HOUSE KEEPING | N/A | N/A | N/A | N/A |
| GAPDH | HOUSE KEEPING | N/A | N/A | N/A | N/A |

FIG. 11C

AVERAGE FOLD CHANGE IN EXPRESSION LEVELS OF GENES

|  |  | MELANOMA CELLS |  | HEM |  |
|---|---|---|---|---|---|
| GENES | AVERAGE FOLD CHANGE AT 400/50 cGy | AVERAGE FOLD CHANGE AT 2400/50 cGy | AVERAGE FOLD CHANGE AT 400/50 cGy | AVERAGE FOLD CHANGE AT 2400/50 cGy |
| AIF | 5 | 15 | -5 | -3 |
| FAS | 10 | 15 | 2 | 3 |
| FAS L | 15 | 28 | 5 | 8 |
| PARP1 | -10 | -5 | -1 | -3 |
| MDM2 | -5 | -20 | 2 | 3 |
| MDM4 | -6 | -34 | 4 | 6 |
| CCND1 (CDK1) | 4 | -15 | 5 | 8 |

HEM-COLONY ASSAY VS # RADIATIONS @50 cGy

| # RADIATIONS | 0 | 1 | 2 | 3 | 4 |
|---|---|---|---|---|---|
| CONTROL/400 | 100 | 73 | 60 | 78 | 71 |
| CONTROL/2400 | 100 | 67 | 58 | 61 | 58 |
| OLIGOMYCIIN/400 | 63 | 48 | 40 | 47 | 43 |
| OLIGOMYCIIN/2400 | 63 | 29 | 23 | 38 | 33 |
| ROTENONE/400 | 56 | 33 | 37 | 36 | 33 |
| ROTENONE/2400 | 56 | 28 | 24 | 20 | 16 |

FIG. 16
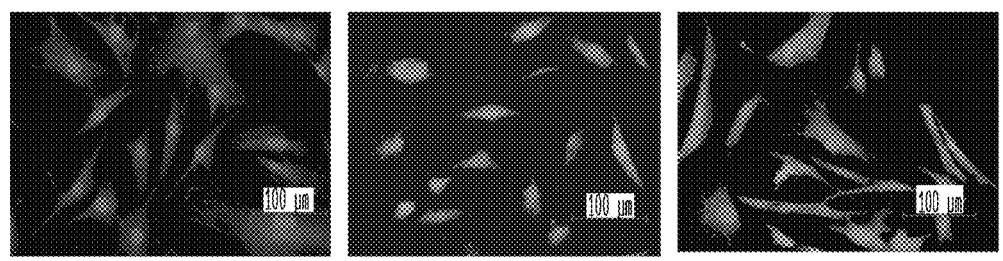
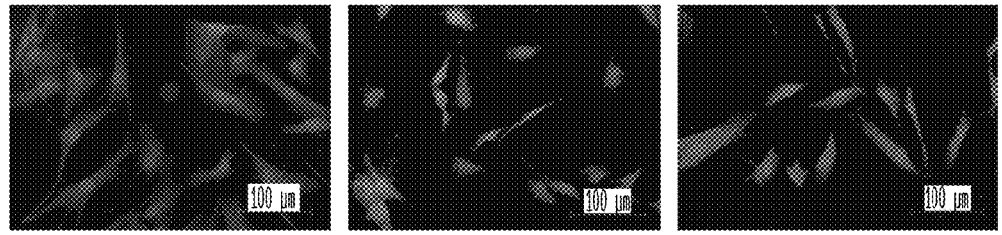
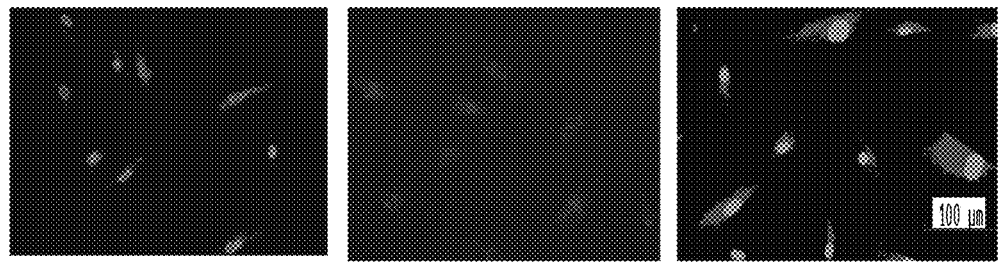

METHOD FOR TREATING SKIN CANCER USING RADIATION THERAPY

CROSS-REFERENCE TO RELATED APPLICATION

This application claims the benefit of priority to U.S. Provisional Application No. 61/923,994, filed Jan. 6, 2014, the content of which is incorporated by reference herein in its entirety.

FIELD OF THE INVENTION

The described invention relates to apparatus and methods for treating a cancer, including malignant melanoma, and to such apparatus and methods for killing cancer cells using radiation therapy.

BACKGROUND OF THE INVENTION

Skin cancer is the most common form of cancer in the U.S., with more than 3.5 million skin cancers diagnosed annually (Rogers, H. W. et al., "Incidence of nonmelanoma skin cancer in the United States, 2006." Arch. Dermatol. 2010; 146(3): 283-287). There are three (3) major types of skin cancer: (1) basal cell carcinoma; (2) squamous cell carcinoma; and (3) melanoma.

Basal cell carcinoma is the most common type of skin cancer in humans. These cancers tend to grow slowly and rarely spread to nearby lymph nodes or to distant parts of the body (www.cancer.org). Treatment methods include simple excision, radiation therapy and chemotherapy among others (www.cancer.org).

Squamous cell carcinoma grows and spreads more than basal cell cancers. This cancer is more likely to invade fatty tissues just beneath the skin and is more likely to spread to lymph nodes and/or distant parts of the body, although this is still uncommon (www.cancer.org). Treatment methods include excision, radiation therapy, systemic chemotherapy and lymph node dissection (www.cancer.org).

Malignant melanoma is a highly aggressive, chemo-resistant, less radio-responsive and lethal malignant neoplasm which is responsible for 60-80% mortality among all skin cancers, with a 5 year survival rate of 14%. J Clin Pathol. 2013 Mar. 23. [Epub ahead of print] Molecular biology of normal melanocytes and melanoma cells. Bandarchi B, Jabbari C A, Vedadi A, Navab R. Radiotherapy is included among the choice of treatments after the surgical treatment options to reduce the rate of recurrence, local control and limiting metastasis to bone or brain. Forschner A, Heinrich V, Pflugfelder A, Meier F, Garbe C, Clin Dermatol. 2013 May-June; 31(3):282-9. doi: 10.1016/j.clindermatol.2012.08.009. It accounts for only 4% of all skin cancer cases but causes more than 75% of all skin cancer deaths. Levine, Steven M., and Richard L. Shapiro. "Surgical Treatment of Malignant Melanoma: Practical Guidelines." *Dermatologic clinics* 30.3 (2012): 487-501. In 2012, there were more than 75,000 diagnosed cases of melanoma, of which more than 9,000 cases were fatal. Siegel, R., Naishadham, D. and Jemal, A. (2012), Cancer statistics, 2012. CA: A Cancer Journal for Clinicians, 62: 10-29. Melanoma incidence and casualty rates have been consistently increasing in the United States ever since 1981. Currently, the national incidence rate of melanoma in Caucasian women younger than the age of 44 is increasing by 6.1% annually, reflecting the popular trend among young women of use of tanning booths and salons. Little, E. G., and M. J. Eide. "Update on the current state of melanoma incidence." *Dermatologic clinics* 30.3 (2012): 355. Cancer registry data indicates that Caucasians have the highest age-adjusted rates of melanoma. Wu, Xiao-Cheng, et al. "Racial and ethnic variations in incidence and survival of cutaneous melanoma in the United States, 1999-2006." *Journal of the American Academy of Dermatology* 65.5 (2011): S26-e1. It has been recently reported that tanning is a prevalent practice in America, with tanning rates in the teenage girl group approaching almost 40%. Balk, Sophie J., David E. Fisher, and Alan C. Geller. "Teens and Indoor Tanning: A Cancer Prevention Opportunity for Pediatricians." *Pediatrics* 131.4 (2013): 772-785.

Melanoma is categorized into four central subtypes: Superficial Spreading Melanoma (SSM), Lentigo Maligna Melanoma (LMM), Acral Lentiginous Melanoma (ALM), and Nodular Melanoma (NM). SSMs are the most common type of melanoma in the Caucasian population, accounting for 70% of all diagnosed melanoma cases. Longo, Caterina, Alice Casari, and Giovanni Pellacani "Superficial spreading melanoma." *Reflectance Confocal Microscopy for Skin Diseases*, Springer Berlin Heidelberg 2012. 151-178. Thin lesions are predominantly in a radial growth phase for months and years before reaching vertical growth. Garbe, Claus, et al. "Diagnosis and treatment of melanoma: European consensus-based interdisciplinary guideline." *European Journal of Cancer* 46.2 (2010): 270-283.

Among the genetic factors, BRAF V600E is the most common mutation associated with development of melanoma and is present in greater than 50% of all melanoma cases. Colombino M., et al., BRAF/NRAS Mutation Frequencies Among Primary Tumors and Metastases in Patients with Melanoma. J Clin Oncol. 2012 Jul. 10; 30(20):2522-9. Epub 2012 May 21; McCubrey et al. *Adv Enzyme Regul.* 2006; 46:249-279. Armelle Calipel, Gaelle Lefevre, Celio Pouponnot, Frédéric Mouriaux, Alain Eychène and Frédéric Mascarelli. Mutation of B-Raf in Human Choroidal Melanoma Cells Mediates Cell Proliferation and Transformation through the MEK/ERK Pathway. J. Biological Chem. 2003. Functions of BRAF include regulation of cell growth, differentiation, and survival. Davies H., et al., Mutations of the BRAF gene in human cancer. Nature 2002. BRAF is a protein kinase and acts as the MAPKKK (W. Kolch, Meaningful relationships: the regulation of the Ras/Raf/MEK/ERK pathway by protein interactions, Biochem J. 2000) in the ERK pathway, an extracellular-signal-regulated kinase network. Eckerle Mize D., Bishop M., Resse E., Sluzevich J. In: Riegert-Johnson D L., Boardman L A., Hefferon T., Roberts M, editors. Familial Atypical Multiple Mole Melanoma Syndrome. Cancer Syndromes [Internet]. Bethesda (Md.): National Center for Biotechnology Information (US); 2009. The mutation at the v600E position causes the amino acid valine to become replaced with glutamic acid, a phosphomimetic, leading to hyperactive kinase activity. FAMMM (Family Atypical Multiple Mole Melanoma Syndrome) is a condition in which a person from a cutaneous melanoma family gets a large number of atypical nevi. Rafehi H., Orlowski C., Georgiadis G T., Ververis K., El-Osta A., Karagiannis "Clonogenic assay: adherent cells," J. Vis Exp. 2011 Mar. 13; (49). pii: 2573. doi: 10.3791/2573. It has been acknowledged that several cases of melanoma within a family are connected to autosomal dominant inheritance. Host Risk Factors, Ultraviolet Index of Residence, and Incident Malignant Melanoma In Situ Among US Women and Men; Andrew C. Walls, Jiali Han, Tricia Li and Abrar A. Qureshi*, 2012. Other higher risk factors include appearance of multiple nevi on extremities, family history of melanoma, dysplastic nevi syndrome, severe and persistent sunburns and hair color. Balch C. M., Soong S. J., Gershenwald J. E., et al. Prognostic factors analysis of 17,600 melanoma patients: Validation of the American Joint Committee on Cancer melanoma staging system. J Clin Oncol 2001; 19:3622-3634.

After melanoma has been diagnosed, there are five standard types of treatment used: surgery, chemotherapy, biologic therapy, targeted therapy, and radiation therapy. Surgical excisions are an early treatment method utilized for patients with thin, non-invasive lesions; excisional biopsies are conducted for easy histological evaluation and assessing excision margins of the remaining tumor. Stevens, Graham, and Angela Hong. "Radiation therapy in the management of cutaneous melanoma" Surgical Oncology Clinics of North America 15.2 (2006): 353-371.

Melanoma has a high potential for systemic metastasis. Incorporation of radiotherapy in management of melanoma is important since metastasis often occurs in the CNS of the patients with a failing response to systemic therapy in most cases. Stevens G, McKay M J, Lancet Oncol. 2006 July; 7(7):575-83. Dispelling the myths surrounding radiotherapy for treatment of cutaneous melanoma; Mohammad K Khan, Niloufer Khan, Alex Almasan, and Roger Macklis. Future of radiation therapy for malignant melanoma in an era of newer, more effective biological agents, OncoTargets Thera. 2011; 4: 137-148.

Generally, advancements in radiation therapy have led to delivery techniques incorporating a high degree of computer control. Shepard, David M., et al. "Optimizing the delivery of radiation therapy to cancer patients." Siam Review 41.4 (1999): 721-744. Developments in imaging technology have allowed an advanced level of complexity to be integrated into radiotherapy treatment planning systems. Bucci, M. Kara, Alison Bevan, and Mack Roach "Advances in radiation therapy: conventional to 3D, to IMRT, to 4D, and beyond" CA: a cancer journal for clinicians 55.2 (2005): 117-134. Radiation therapy, including intensity modulated radiation therapy, enables clinical application of highly conformal dose distributions. Ezzell, Gary A., et al. "Guidance document on delivery, treatment planning, and clinical implementation of IMRT: Report of the IMRT subcommittee of the AAPM radiation therapy committee." Medical physics 30 (2003): 2089. Each radiation therapy field contains small, irregular, off-axis fields, resulting in delivery of isodose distributions more conformal than conventional treatment plans. Palta, Jatinder R., Chihray Liu, and Jonathan G. Li. "Quality assurance of intensity-modulated radiation therapy." International Journal of Radiation Oncology* Biology* Physics 71.1 (2008): S108-S112. The intensity of each distributed beamlet is adjusted according to the necessary planning dose objectives. The intensity patterns are then decomposed into multi leaf collimator (MLC) shapes for sequencing. Broderick, Maria, Michelle Leech, and Mary Coffey "Direct aperture optimization as a means of reducing the complexity of Intensity Modulated Radiation Therapy plans" Radiat Oncol 4.8 (2009): 1-7. Radiotherapy has become increasingly used over the years and is now rapidly being implemented in clinical departments throughout the United States. Purdy, James A "From new frontiers to new standards of practice: advances in radiotherapy planning and delivery" (2007): 18-39.

Past radiation treatments on cancer patients have shown effective coverage of target tumor tissue while reducing exposure to volumes of surrounding normal tissue, even at high dose levels. Zelefsky, Michael J., et al. "Clinical experience with intensity modulated radiation therapy (IMRT) in prostate cancer" Radiotherapy and Oncology 55.3 (2000): 241-249. Multiple static multileaf collimator segments used in combination with radiation therapy have proven to be an efficient method for attaining uniform dose in cancer treatment. Kestin, Larry L., et al. "Intensity modulation to improve dose uniformity with tangential breast radiotherapy: initial clinical experience" International Journal of Radiation Oncology* Biology* Physics 48.5 (2000): 1559-1568.

Over the years, machines based on kilovoltage x-rays and gamma rays have been replaced by linear particle accelerators (LINACs) that produce up to 18 MV of energy for conformal therapy Xu, X. George, Bryan Bednarz, and Harald Paganetti "A review of dosimetry studies on external-beam radiation treatment with respect to second cancer induction." Phys. Med. Biol 53 (2008): R193-R241. Publications involving radiation treatments and radiation therapy report usage of LINACs set at a common 400 cGy/min dose rate. Wolff, Dirk, et al. "Volumetric modulated arc therapy (VMAT) vs. serial tomotherapy, step-and-shoot IMRT and 3D-conformal RT for treatment of prostate cancer." Radiotherapy and Oncology 93.2 (2009): 226-233. Adams, Elizabeth J., et al. "Clinical implementation of dynamic and step-and-shoot IMRT to treat prostate cancer with high risk of pelvic lymph node involvement" Radiotherapy and oncology 70.1 (2004): 1-10. Gierga, David P., et al. "Quantification of respiration-induced abdominal tumor motion and its impact on IMRT dose distributions" International Journal of Radiation Oncology* Biology* Physics 58.5 (2004): 1584-1595. The Varian TrueBeam radiotherapy system, by Varian Medical Systems of Palo Alto, Calif., has been tested and shown to be feasible for delivering radiation therapy to various tumor sites using flattening filter free (FFF) beams. Scorsetti, Marta, et al. "Feasibility and early clinical assessment of flattening filter free (FFF) based stereotactic body radiotherapy (SBRT) treatments" Lung34 (2011): 48. The TrueBeam system has been tested to show consistent dose accuracy efficiency even as dose rate increases. Dose accuracy has been tested to be maintained even at dose rates as high as 2,400 cGy/min. Li, Ji, et al. "Improvements in dose accuracy delivered with static-MLC IMRT on an integrated linear accelerator control system" Medical Physics 39 (2012): 2456.

Integration of radiation therapy into the management plan of melanoma can enable improvement of loco-regional control and alleviation of symptoms from metastatic disease. Modern day linear accelerators with flattening filter free mode may be used to increase dose rate capabilities producing advantages over conventional radiotherapy such as the capability for increasing the delivery of radiation at rates per minute not previously available. In addition, the image guidance, along with volumetric arc therapy capabilities, exhibit improved target conformity, sparing normal tissue surrounding the lesion and dose escalation in the target volume. Its ability to deliver the doses in concave isodose profiles to minimize the injury to the normal surrounding tissue is considered as a significant improvement in the area of radiation oncology. Calabro A., Singletary S. E., Balch C. M., Patterns of relapse in 1001 consecutive patients with melanoma nodal metastases. Arch Surg. 1989; 124:1051-1055. Byers R. M., The role of modified neck dissection in the treatment of cutaneous melanoma of the head and neck, Arch Surg 1986; 121:1338-1341. Kirkwood J. M., Ibrahim J. G., Sosman J. A., et al. High-dose interferon alfa-2b significantly prolongs relapse-free and overall survival compared with the GM2-KLH/QS-21 vaccine in patients with resected stage IIB-III melanoma. Results of intergroup trial E1694/S9512/C509801. J. Clin Oncol. 2001; 19:2370-2380. Florian Sterzing et al: Radiobiological investigations of dose rate effects on IMRT.

The emergence of Intensity Modulated Radiation Therapy (IMRT), using advanced software to plan a precise dose of radiation, based on tumor size, shape and location is helpful in treatment of melanoma. A computer-controlled linear accelerator may be used to deliver radiation in sculpted doses that match the exact 3D geometrical shape of the tumor, including concave and complex shapes. Local dose elevation with radiation therapy has led to good local and distant tumor control as well as minimization of toxicity due to radiation exposure for past melanoma patients. Combs, Stephanie E., et al. "Local high-dose radiotherapy and sparing of normal tissue using intensity-modulated radiotherapy (IMRT) for mucosal melanoma of the nasal cavity and paranasal sinuses" *Strahlentherapie und Onkologie* 183.2 (2007): 63-68. Hypofractionated radiation used as an adjuvant therapy method for melanoma treatment has been proven to enable a high rate of in-field control and low risk of toxicity. Hallemeier, C. L., et al. "Adjuvant Hypofractionated Intensity Modulated Radiation Therapy (IMRT) After Resection of Regional Lymph Node (LN) Metastases in Patients With Malignant Melanoma of the Head and Neck" *International Journal of Radiation Oncology\* Biology\* Physics* 84.3 (2012): S505-S506.

A series of close to diploid human melanoma cell lines were shown to be highly resistant to UV radiation. Chalmers, A H et al, "Resistance of Human Melanoma Cells to Ultraviolet Radiation," Cancer Res. 1976; 36: 1930-1934. It was suggested that such resistance could confer a proliferative advantage to the tumor cells under conditions of irradiation. Id.

The described invention provides a method to treat cancer by radiation therapy in which a high dose rate is used to deliver ionizing radiation at a low dose in the 25-50 centigray (cG) range, i.e., 6-10 times lower than a standard irradiation dose, which is effective to kill cancer cells 4-5 times more effectively than a standard dose of ionizing radiation.

SUMMARY OF THE INVENTION

The described invention provides methods for treating a skin cancer in a subject while maintaining survival of normal cells.

According to one aspect, the described invention provides a method for treating a skin cancer in a subject comprising irradiating the skin cancer with a total dose not to exceed 1 Gy at a dose rate of 2,400 mu/min, wherein the total dose at the dose rate of 2,400 mu/min is effective to decrease the cell survival percentage (%) of the skin cancer while maintaining the survival percentage (%) of normal cells.

According to another aspect, the described invention provides a method for inducing apoptosis in skin cancer cells comprising irradiating the skin cancer cells with a total dose not to exceed 1 Gy at a dose rate of 2,400 mu/min, wherein the total dose at the dose rate of 2,400 mu/min is effective to up-regulate gene expression levels of apoptotic genes in the skin cancer cells while maintaining gene expression levels of apoptotic genes in normal cells.

According to one embodiment, the skin cancer is selected from the group consisting of basal carcinoma, squamous carcinoma, and melanoma. According to another embodiment, the skin cancer is melanoma. According to another embodiment, the skin cancer is a radiation resistant skin cancer.

According to one embodiment, the skin cancer cells are selected from the group consisting of basal carcinoma cells, squamous carcinoma cells, melanoma cells. According to another embodiment, the skin cancer cells are melanoma cells. According to another embodiment, the skin cancer cells are radiation resistant skin cancer cells.

According to one embodiment, the total dose is selected from the group consisting of 0.25 Gy, 0.5 Gy, 0.75 Gy, and 1 Gy. According to another embodiment, the total dose is 0.5 Gy.

According to one embodiment, the normal cells are epidermal melanocytes.

According to one embodiment, the method further comprises a chemotherapeutic agent. According to another embodiment, the chemotherapeutic agent is a mitochondrial inhibitor. According to another embodiment, the mitochondrial inhibitor is Oligomycin. According to another embodiment, the mitochondrial inhibitor is Rotenone. According to another embodiment, the chemotherapeutic agent is paclitaxel.

According to one embodiment, the apoptotic genes are selected from the group consisting of AIF, FAS, FASL, PARP1, MDM2, MDM4.

According to one embodiment, the expression levels of the apoptotic genes are measured using quantitative reverse transcriptase polymerase chain reaction (qRT-PCR).

BRIEF DESCRIPTION OF THE DRAWINGS

For a more complete understanding of the present disclosure, reference is made to the following detailed description of exemplary embodiments considered in conjunction with the accompanying drawings.

FIG. 2B is a set of comparative graphs of cell proliferation vs. radiation dose and rate and the presence/absence of mitochondrial inhibitors for two different types of cells.

FIG. 5B is a table of RT-PCT results for two types of cells having been exposed to two different rates of radiation.

FIGS. 11(A)-11(C) are tables of average fold changes of targeted genes observed in two different types of cells radiated at two different rates.

FIG. 16 is a series of images of a mitotracker assay of HEM cells that have been subjected to radiation at two different rates and selectively treated with different mitochondrial inhibitors.

DETAILED DESCRIPTION OF THE INVENTION

Definitions

Figure 1A:
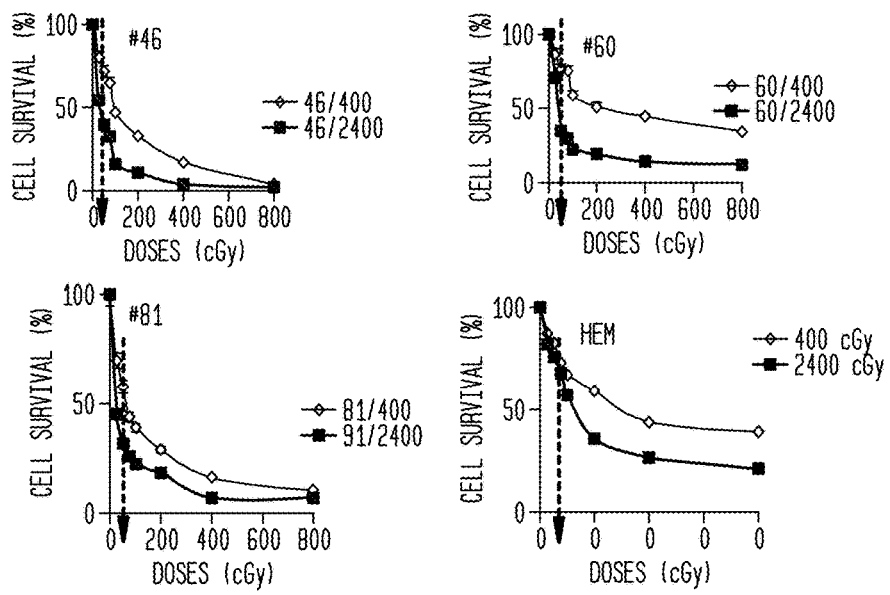
FIG. 1A is a series of comparative graphs of cell survival percentage vs. radiation dose and rate for four different types of cells.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligomerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

The term "centigray (cGy)" as used herein refers to a derived metric (SI) measurement unit of absorbed radiation dose of ionizing radiation, e.g. X-rays. The SI prefix centi stands for one hundredths. The centigray is equal to one hundredth of a gray (0.01 Gy), and the gray is defined as the absorption of one joule of ionizing radiation by one kilogram (1 J/kg) of matter, e.g. human tissue.

The disclosed subject matter relates to a method for treating cancer cells comprising administering ionizing radiation at a high dose rate and delivering a low radiation dose per treatment. The described invention recognizes that an unconventionally high dose rate can increase the rate and percentage of apoptosis in malignant cells, a beneficial outcome.

According to one aspect of the described invention, a dose rate greater than that which is conventionally given, but sustained for a shorter period, such that the total radiation absorbed does not exceed conventional limits, more effectively kills cancer cells without unduly increasing the destruction of normal cells compared to conventional dose rates. This enhanced effectiveness is noteworthy with respect to radio-resistant cancers.

According to one embodiment, the cancer cells are resistant to conventional ionizing radiation protocols.

According to another embodiment, the total dose is measured over one radiation treatment. According to another embodiment, the total dose does not exceed 8.0 Gy. According to another embodiment, the total dose does not exceed 0.5 Gy. According to another embodiment, the rate of irradiation for each radiation treatment does not exceed 2,400 mµ/min. According to another embodiment, a plurality of radiation treatments are administered to the cells.

According to another embodiment, the method is effective to decrease cell proliferation of the cancer cells.

According to another embodiment, the method is effective to increase expression/upregulate nuclear apoptosis genes, decrease expression/downregulate DNA repair genes, or a combination thereof.

According to another embodiment, the method is effective to increase expression/upregulate nuclear apoptosis genes (e.g., Apoptosis-inducing factor (AIF), Fas, a member of the TNF-receptor superfamily, FasL, which is often transcriptionally inactive, but becomes activated in many forms of transcription/translation dependent apoptosis (Pinkoski, M J, Green, D R, "Fas ligand, death gene," Cell Death Differ. 6(12): 1174-81 (1999)), poly (ADP-ribose) polymerase 1(Parp1), Mdm3, or Mdm4).

According to another embodiment, the method is effective to decrease expression/downregulate DNA repair genes (e.g., mutS homolog 2, colon cancer, nonpolyposis type 1 (E. coli)(MSH2); cyclin-dependent kinase 1 (CCND 1); cyclin-dependent kinase 2 (CCND2).

According to another embodiment, the method further comprises potentiating a selective adjunct therapy of the cancer while preserving normal cells.

According to another embodiment, the adjunct therapy is a chemotherapy comprising at least one chemotherapeutic agent.

According to another embodiment, the chemotherapeutic agent comprises a mitochondrial inhibitor agent.

According to another embodiment, the mitochondrial inhibitor agent is oligomycin, rotenone, or a combination thereof.

According to another embodiment, the chemotherapeutic agent comprises a mitotic inhibitor.

According to another embodiment, the mitotic inhibitor is Paclitaxel.

According to another embodiment, the radiation is administered using intensity modulated radiation therapy.

According to another embodiment, the irradiated cancer cells comprise melanoma cells.

According to another embodiment, the melanoma cells are present on the body of a human subject.

According to another embodiment, the irradiation of cells includes normal cells of the human subject.

According to another embodiment, the method is effective to induce cell death in a greater percentage of the melanoma cells irradiated than in the normal cells irradiated.

According to another embodiment, the percentage of melanoma cells killed by the irradiation exceeds that of the percentage of normal cells killed.

According to another embodiment, the percentage of melanoma cells killed by the irradiation exceeds that of the percentage of normal cells measured within the period of time associated with the average lifespan of normal human epithelial melanocytes (HEM).

According to another embodiment, the method reduces cell proliferation to a greater degree in the melanoma cells irradiated than in the normal cells irradiated.

According to another embodiment, the cells irradiated include radio-resistant cells.

According to another embodiment, the radio-resistant cells include malignant melanoma cells.

According to another embodiment, the mitochondrial inhibitor is administered at a titrated dose of less than or equal to 0.5 µM.

The described invention may also be applied in conjunction with other known chemotherapeutic drugs, including cisplatin and its derivatives, and paclitaxel and its derivatives, for use in adjuvant therapy with radiation.

According to another embodiment, ratios of fibroblast cells to melanoma cells may be assessed to determine an accurate 2-dimensional image of an actual primary melanoma tumor site. Once a realistic histological 2-dimensional culture is obtained, the 2,400 cGy/min dose rate at 50 cGy may be administered to achieve melanoma cell kill in tissue having both normal fibroblasts and melanoma cells.

In accordance with an embodiment of the described invention, the apoptotic effects between two dose rates, 400 mu/min and 2400 mu/min on melanoma cells with 10 FFF (Flattening Filter Free mode) TrueBeam™ doses in the amounts of 0.25 Gy, 0.5 Gy, 0.75 Gy, 1 Gy, 2 Gy, 4 Gy and 8 Gy were compared. Normal epidermal melanocytes were used as controls. Mitochondrial inhibitors Oligomycin and Rotenone were also used to assess the combinatorial effect on apoptosis of melanoma cells. According to another embodiment, drug targets for melanoma can be developed with reduced lethal effects on surrounding normal cells.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods
Cell Lines and Reagents

Three melanoma cell lines; WC00046, WC00060 and WC00081 were used in these examples, in which WC00046 was the most aggressive cell line (metastatic stage II), WC00060 was least aggressive (stage I, primary tumor site) and WC00081 was the medium aggressive (malignant melanoma primary site), purchased from Coriell Institute of Camden, N.J. The primary HEM (human epidermal melanocytes) was purchased from ScienCell Research Laboratories of Carlsbad, Calif. (#2220). Melanoma cells were grown in RPMI (Invitrogen) with 10% FBS, 1% Penicillin/Streptomycin. HEM cells were grown in Mel-M media (ScienCell Research Laboratories, Catalog number 2201) supplemented with 5 ML, Mel GS (ScienCell Research Laboratories, Catalog number 2252), 2.5 ML FBS (ScienCell Research Laboratories, Catalog number 0002) and 5 ML penicillin/Streptomycin solution (ScienCell Research Laboratories, Catalog number 0503), which is a complete medium designed for optimal growth of normal human dermal-derived melanocytes in vitro.

Mitochondrial Inhibitors

Two mitochondrial inhibitors Oligomycin (Sigma Aldrich # O4876) and Rotenone (Sigma Aldrich #R8875) were used. An optimal concentration of 0.5 uM were used for both melanoma cell lines and HEM added to the growth medium and removed after the irradiation. Dilutions were made in DMSO according to manufacturer's instructions.

Colony Forming Assays

Radiated cells were washed with 1× phosphate buffer saline (PBS), trypsinized and harvested in corning tubes (15 ml, BD Falcon). These cells were serially diluted (1:100, 1:1000, 1:10000) and plated in Petri-dishes (Tissue culture Petri dishes, BD Falcon) with complete media and allowed to grow colonies for 7-21 days. Colonies were stained with Hematoxylin for 30 min after fixing the cells in 100% ethanol for about 20-30 min. Petridishes with stained colonies were washed in water, dried overnight and counts were recorded.

RNA Isolation and Quantitative Real Time PCR

Figure 5A:
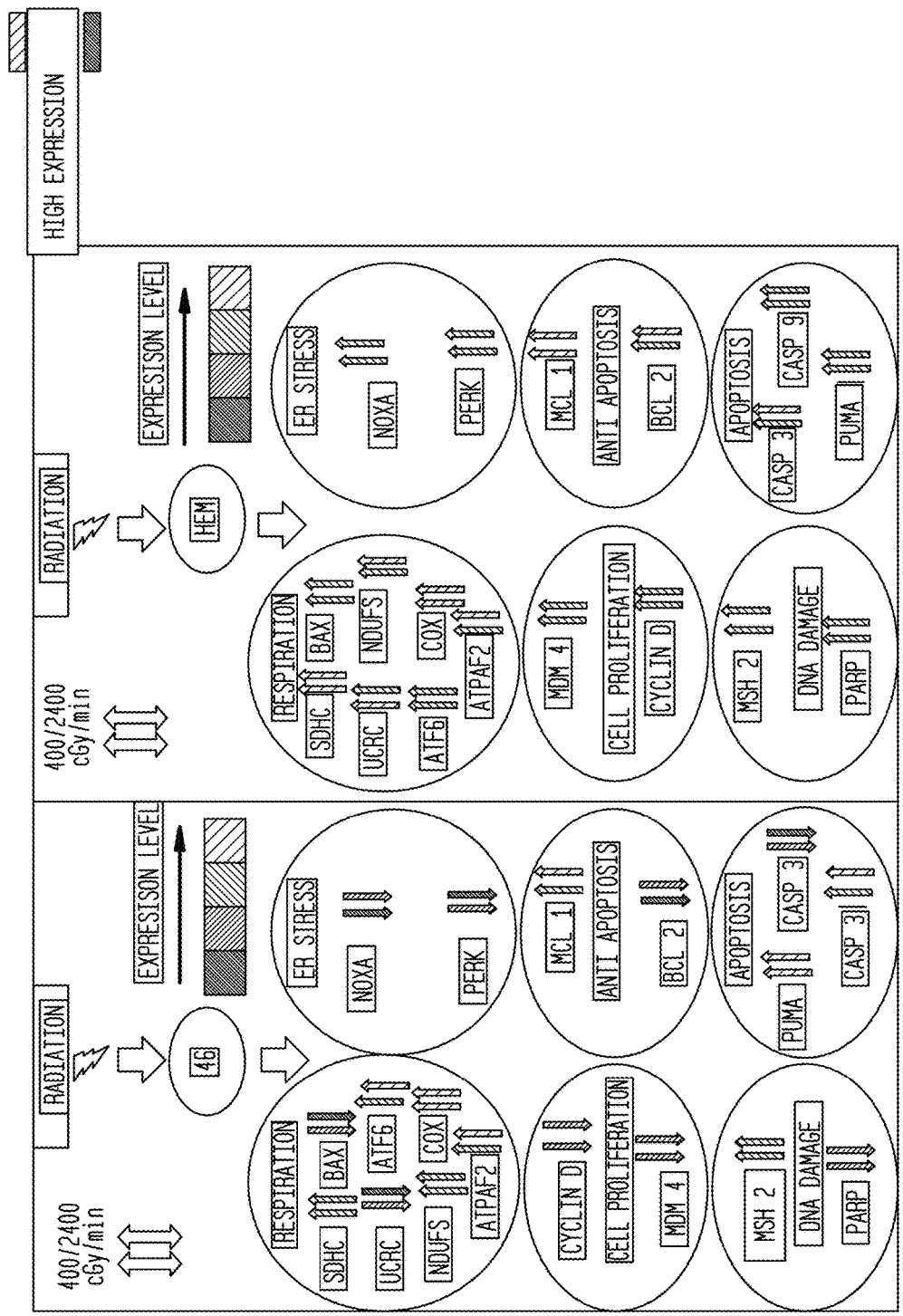
FIG. 5A is a diagram of gene expression for two types of cells after being exposed to radiation.
Figures 6A, 6B:
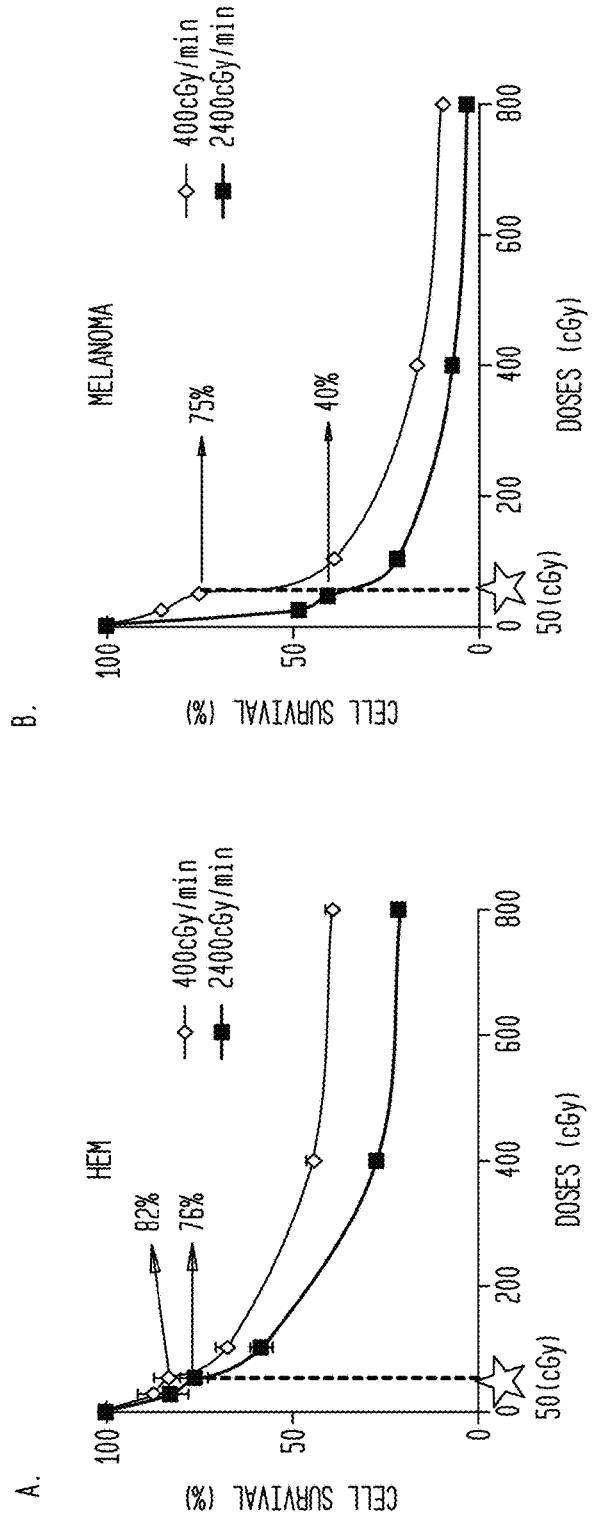
FIGS. 6A and 6B are comparative graphs of cell survival percentage vs. radiation dose and rate for two different types of cells.
Figure 7:
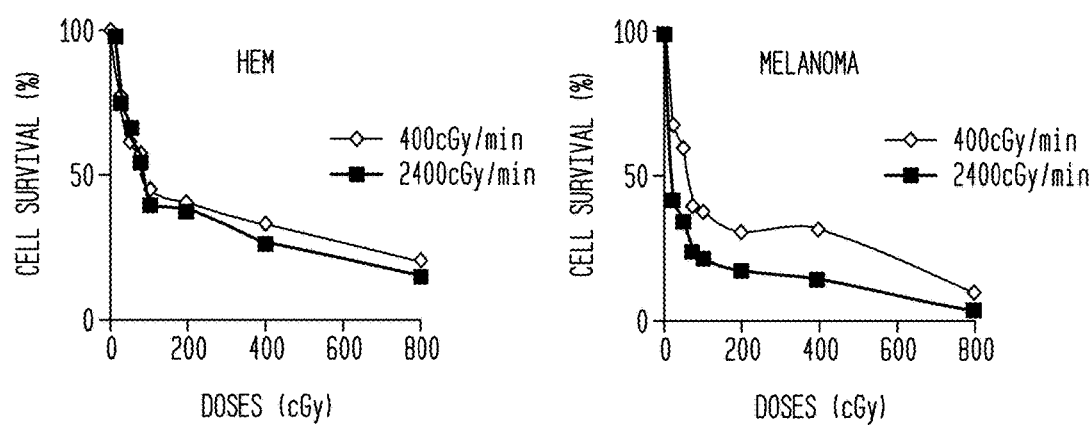
FIG. 7 is a set of comparative graphs of cell survival percentage vs. radiation dose and rate for two different types of cells.
Figure 8:
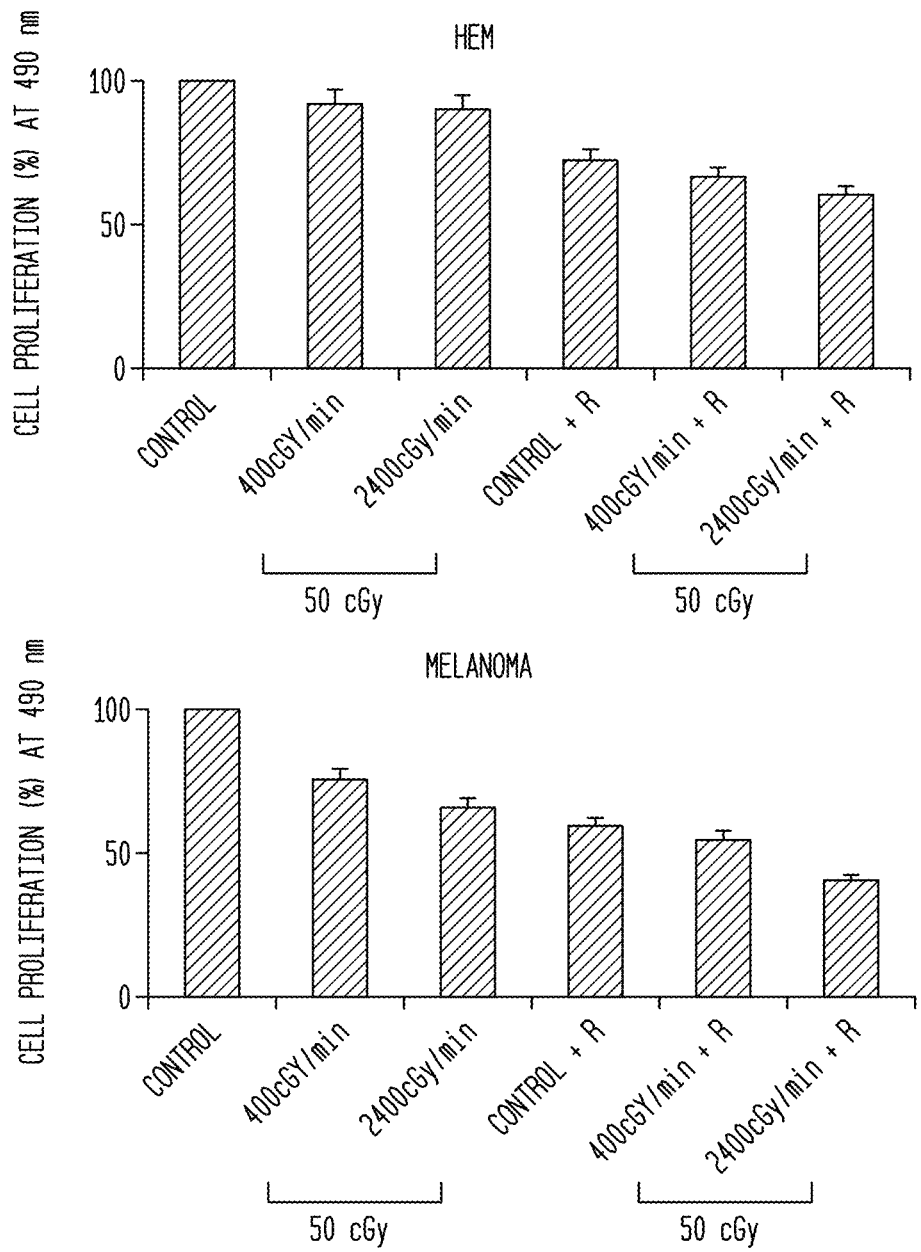
FIG. 8 is a set of comparative graphs of cell proliferation vs. radiation dose and rate and the presence/absence of mitochondrial inhibitors for two different types of cells.
Figure 9:
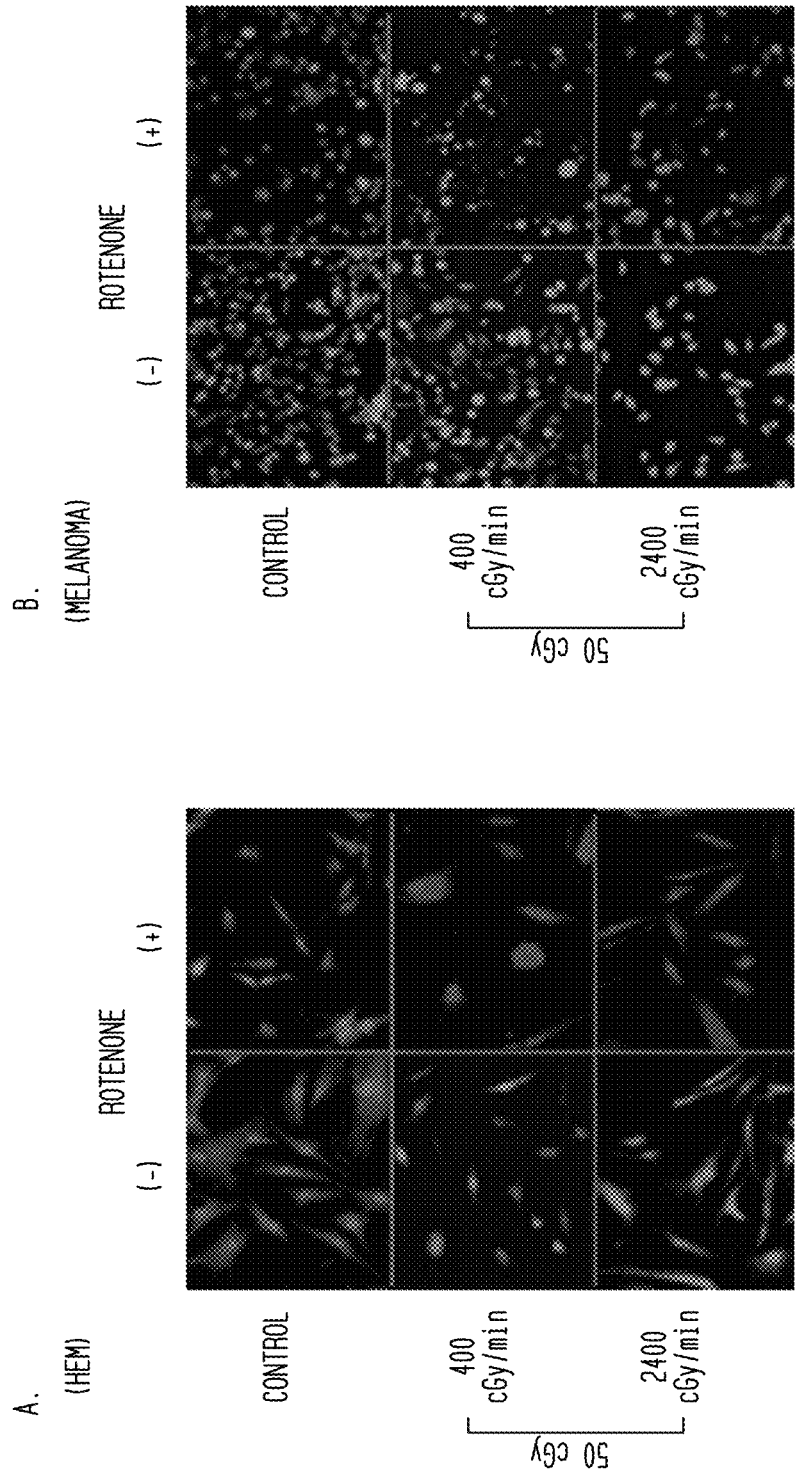
FIG. 9 is a series of images of a mitotracker assay of two types of cells that have been subjected to radiation at two different rates and selectively treated with a mitochondrial inhibitor.
Figure 10:
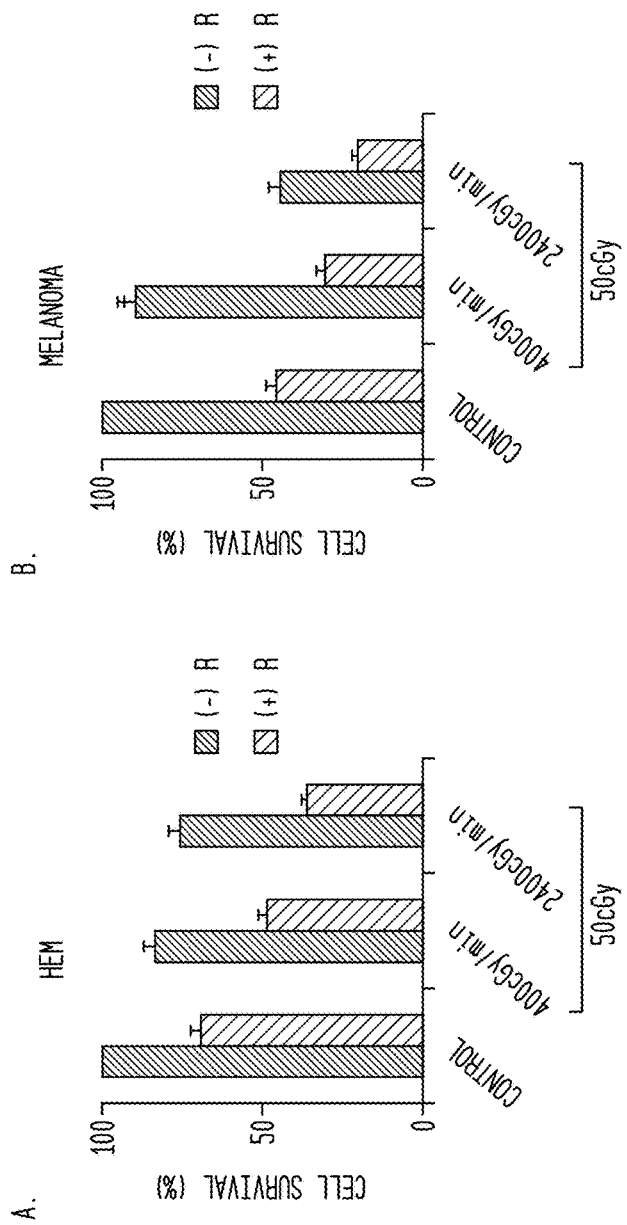
FIG. 10 is a series of comparative graphs of cell survival percentage vs. radiation dose and rate and the presence/absence of a mitochondrial inhibitor for different types of cells.
Figure 12:
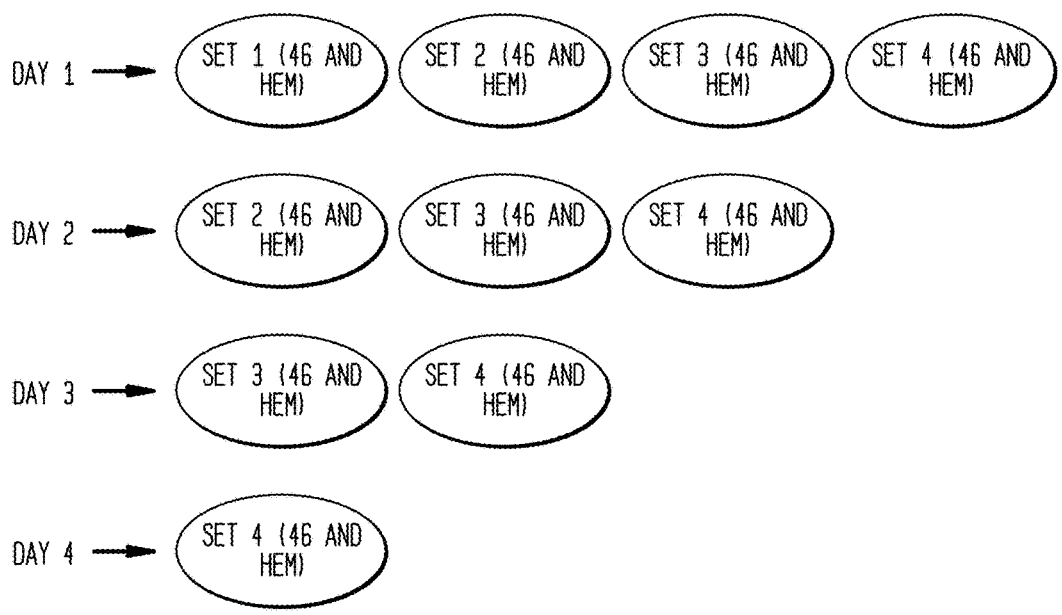
FIG. 12 is a diagram of a radiation treatment schedule for four sets of two different cells.
Figure 13:
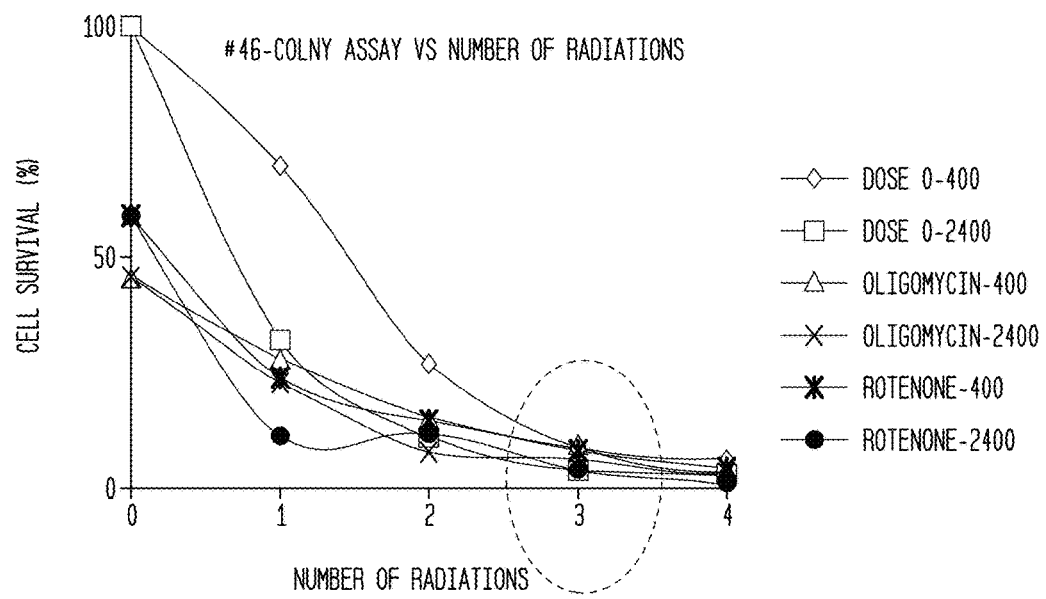
FIG. 13 is a graph and associated data table of cell survival percentage vs. number of radiations and radiation rate for melanoma cells selectively treated with two different mitochondrial inhibitors as revealed by a colony assay.
Figure 14:
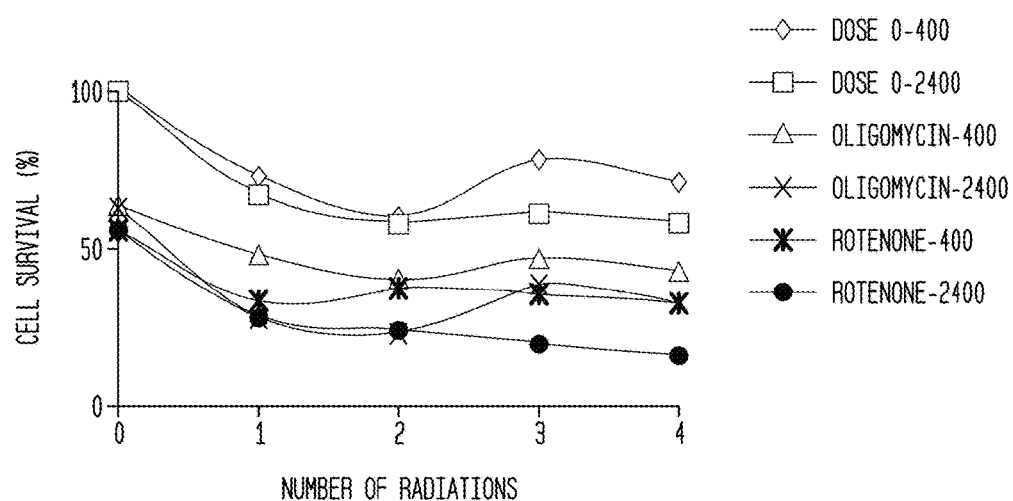
FIG. 14 is a graph and associated data table of cell survival percentage vs. number of radiations and radiation rate for human epithelial melanocytes (HEM) cells selectively treated with different mitochondrial inhibitors as revealed by a colony assay.
Figure 15:
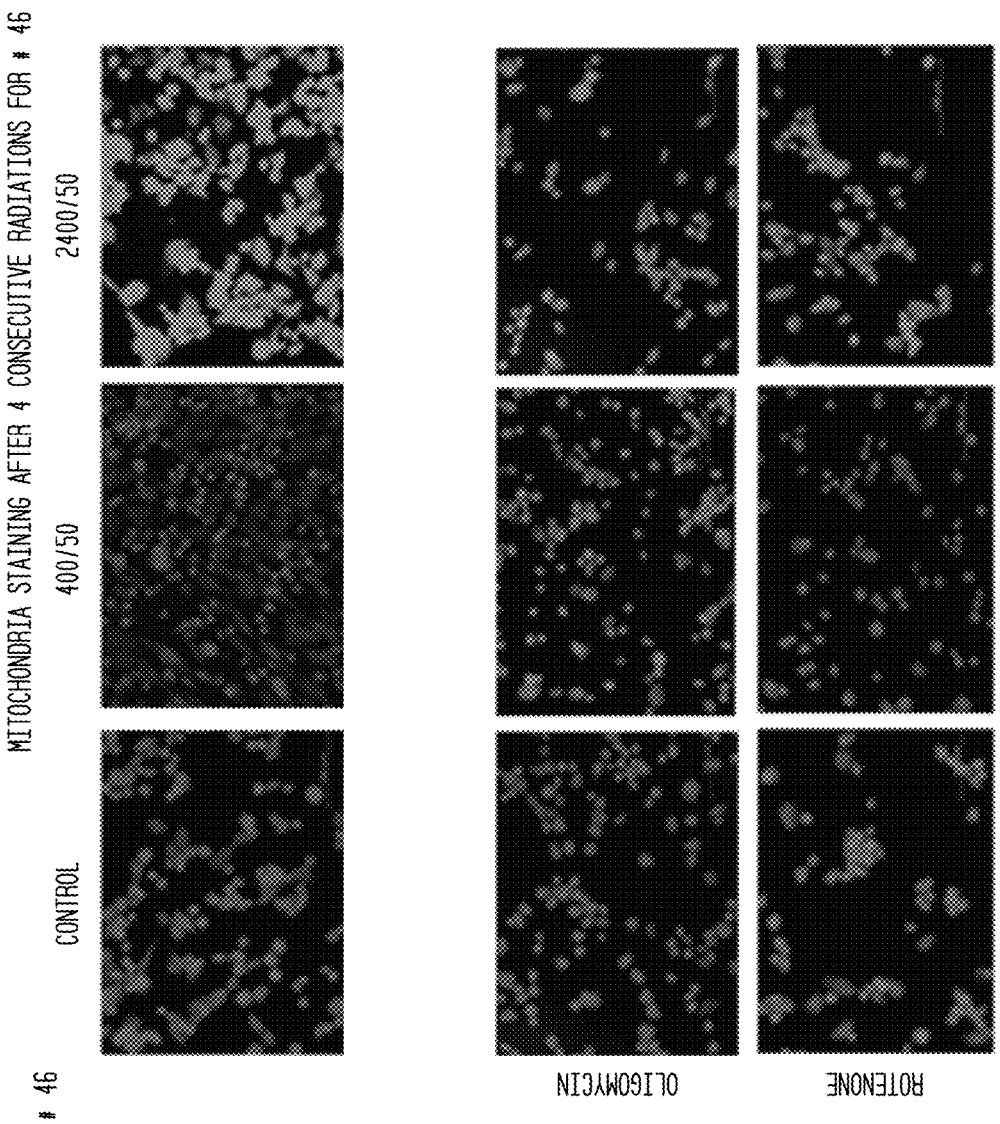
FIG. 15 is a series of images of a mitotracker assay of melanoma cells that have been subjected to radiation at two different rates and selectively treated with two different mitochondrial inhibitors.
Figure 17:
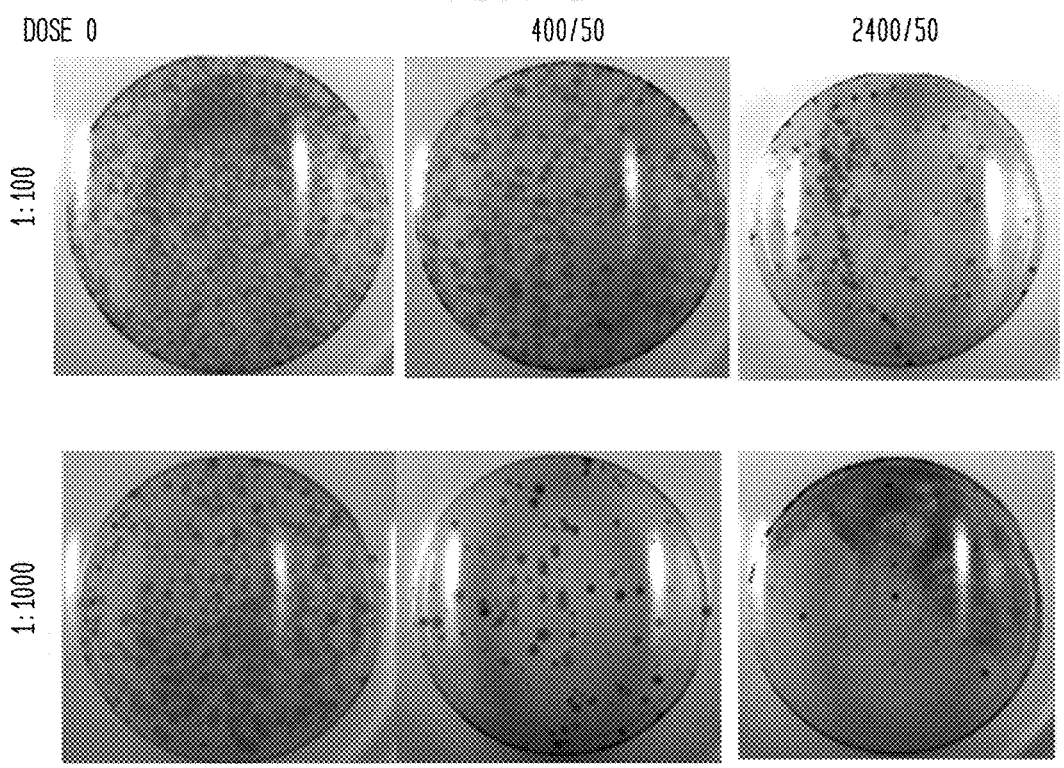
FIG. 17 is a series of images of cell colonies that had been irradiated at different rates.
Figure 18:
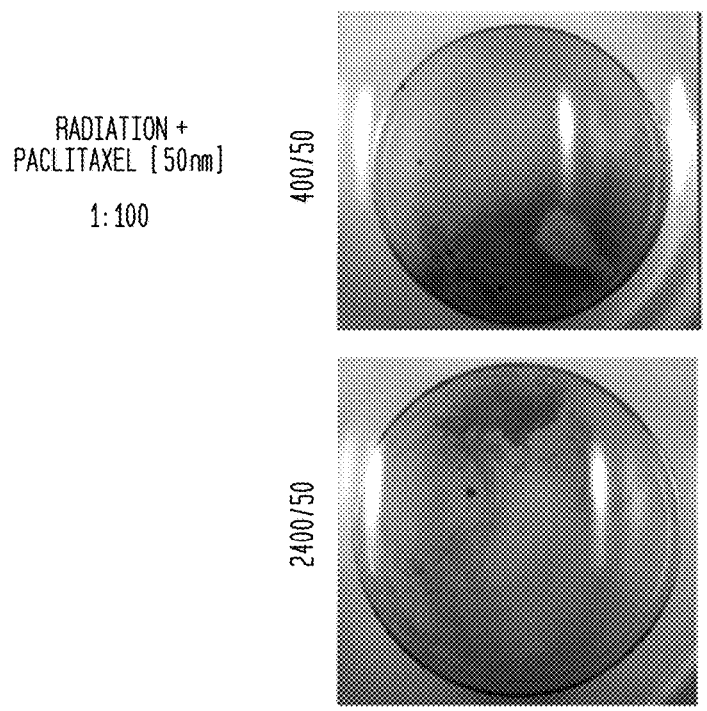
FIG. 18 is a series of images of cell colonies that had been irradiated at different rates and exposed to a chemotherapeutic drug.

RNA was isolated with TRIZOL reagent (Invitrogen), and selected genes were amplified by qPCR using SYBR green (Qiagen) incorporation during the amplification reaction. Primer sequences are given in the table shown in FIG. 5B. Q-RT-PCR was performed on the FAST Model 7900HT RT-PCR machine (Applied Biosystems, Foster City, Calif.) to determine relative mRNA expression levels of target genes. Each 20 ul reaction volume contained 30 ng cDNA template, 10 ul 2× Power SYBR Master Mix (Applied Bio systems, Foster City, Calif.), 1 ul 10 uM forward primer, 1 ul 10 uM reverse primer. As per manufacturer's recommendations, PCR conditions were set in standard mode for Power SYBR qRT-PCR performed on a FAST 96-well block using MicroAmp Fast Optical 96-Well Reaction Plate with Barcode (Applied Biosystems, Foster City, Calif.): denaturation at 95° C. for 10 minutes, followed by 40 cycles at 95° C. for 15 sec and 60° C. for 1 minute and a dissociation stage comprised of one cycle at 95° C., 15 sec, 60° C., 15 sec and 95° C., 15 sec. Using GAPDH and B2M as the endogenous gene references, qRT-PCR data were analyzed using the SDS 7900HT software v2.2.2 application to determine the comparative threshold cycle (Ct) method ($2^{-\Delta\Delta Ct}$). Fold change and standard deviation were calculated and represented by bar graphs (data not shown).

Migration Assay

Migration assay was carried out using QCM TM 24-well Collagen Based Cell Invasion Assay kit (Chemicon International) as per manufacturer's instructions. Cells were counted using Beckman Coulter Counter and results of the assay were represented in a bar chart.

Cell Proliferation Assay

MTT assay was carried out to measure the cell proliferation in radiated cells. Cells were seeded in 94 well plate and incubated with MTT assay reagent (tetrazolium dye). MTT assay is based on the ability of metabolically active cells to reduce the yellow tetrazolium salt (MTT) by to form insoluble purple formazan crystals, which are solubilized by the addition of a detergent and quantified (i.e., color). The MTT Cell Proliferation Assay measures the cell proliferation rate and conversely, when metabolic events lead to apoptosis or necrosis, the reduction in cell viability. The number of assay steps has been minimized as much as possible to expedite sample processing. The MTT Reagent yields low background absorbance values in the absence of cells. For each cell type the linear relationship between cell number and signal produced is established, thus allowing an accurate quantification of changes in the rate of cell proliferation.

Mitotracker Assay

Mitotracker Red CMXRos (Invitrogen-M7512) was used for mitotracker assay. Stock solution was prepared in anhydrous DMSO, and the aliquots were stored in −30° C. Stock solution was diluted with culture media prior to the assay. Cells were treated with Mitotracker working solution (200 nM) and incubated for 15 minutes (37° C., 5% $CO_2$). Labeling solution was removed and cells were washed with 1×PBS followed by fixing with 2% PFA (paraformaldehyde) for 30 minutes at room temperature in dark. Cells were washed with 1×PBS and mounted using DAPI and images were taken immediately.

Statistical Analysis

All experiments were performed a minimum of three times. Data represent the results for assays performed in triplicate or more, and error bars represent 95% confidence intervals (CIs). All statistics were based on continuous variables. For comparisons between two groups, the Student's t test was applied. Drug dose-response curves were analyzed with a nonlinear regression curve fit model. P values of less than 0.05 were considered statistically significant. All statistical tests were two-sided. All statistical analysis and calculations were performed using software STAT View.

Example 1: Effect of Radiation on Melanoma Cells and Normal Cells

In this study, three (3) melanoma cell lines were used to compare the ability of different radiation dose rates to induce effective cell killing. Melanoma cell lines were selected based on their known resistance to radiation therapy. Human epidermal melanocytes (HEM) were used to determine the effect of ionizing radiation on normal cells.

Melanoma cell lines WC00046, WC00060 and WC00081 (purchased from Coriell Institute of Camden, N.J.) were seeded at 5×10⁵ cells in T-25 culture flasks (BD-Falcon, Franklin Lakes, N.J., Catalog #356536 or equivalent) containing either RPMI media (Invitrogen, Carlsbad, Calif., Catalog #11875119 or equivalent) with 10% fetal bovine serum (FBS; ATCC Catalog #30-2020 or equivalent), 1% Penicillin/Streptomycin (GIBCO, Carlasbad, Calif., Catalog #15140 or equivalent) or RPMI media with 10% FBS, 1% Penicillin/Streptomycin, 5 µM Oligomycin (Sigma-Aldrich, St. Louis, Mo., Catalog #04876) or RPMI media with 10% FBS, 1% Penicillin/Streptomycin, 5 µM Rotenone (Sigma-Aldrich, St. Louis, Mo., Catalog #R8875). Human Epidermal Melanocytes (HEM) (ScienCell Research Laboratories, Carlsbad, Calif., Catalog #2220) were seeded at 5×10⁵ cells in a T-25 culture flask (BD-Falcon, Franklin Lakes, N.J., Catalog #356536 or equivalent) containing either Mel-M media (ScienCell Research Laboratories, Carlsbad, Calif., Catalog #2201) or Mel-M media, 5 µM Oligomycin or Mel-M media, 5 µM Rotenone. Cells were allowed to settle and adhere to the T-25 culture flasks by overnight incubation in a humidified incubator at 37° C., 5% $CO_2$. Following incubation, all T-25 culture flasks were irradiated with a TrueBeam™ system (Varian Medical Systems, Palo Alto, Calif.) at doses of 0.25 Gy, 0.5 Gy, 0.75 Gy, 1 Gy, 2 Gy, 4 Gy and 8 Gy using a ten (10) Flattening Filter Free mode for two monitor units (400 mu/min and 2,400 mu/min). Cells were counted and cell survival (%) was recorded two (2) days and seven (7) days post radiation.

Figure 1B:
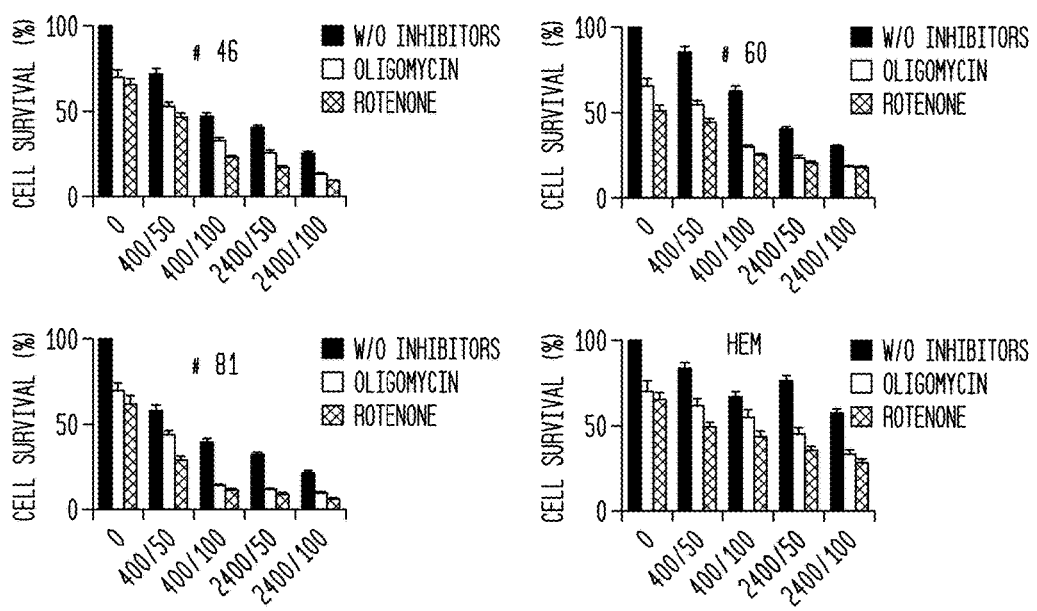
FIG. 1B is a series of comparative graphs of cell survival percentage vs. radiation dose and rate and the presence/absence of mitochondrial inhibitors for four different types of cells.

The results of this study are depicted in FIGS. 1A and 1B.

As shown in FIG. 1A, the cell survival (%) was higher in HEM at lower doses from 0.25 Gy, 0.5 Gy, 0.75 Gy and 1 Gy for both dose rates 2,400 mu/min (76%) and 400 mu/min (83%). For melanoma cell line WC00046 (#46), the cell survival (%) was 40% (p value<0.005), when irradiated at 2,400 mu/min for a total dose 0.5 Gy. For melanoma cell lines WC00060 (#60) and WC00081 (#81), corresponding values were 30% and 35% respectively. This is consistent with previously published studies which indicate that normal body cells are more efficient in repairing DNA damage than tumor cells (Yamamori T., Yasui H., Yamazumi M., Wada Y., Nakamura Y., Nakamura H., Inanami O. "Ionizing radiation induces mitochondrial reactive oxygen species production accompanied by upregulation of mitochondrial electron transport chain function and mitochondrial content under control of the cell cycle checkpoint." Free Radic Biol Med. 2012 Jul. 15; 53(2):260-70. doi: 10.1016/j.freeradbiomed.2012.04.033. Epub 2012 May 8). These results indicate that a low total dose (0.5 Gy) at a dose rate of 2,400 mu/min is effective to kill melanoma cells while being less toxic on HEM.

FIG. 1B shows the cell survival (%) of melanoma cells and HEM grown in the presence of the mitochondrial inhibitors Oligomycin and Rotenone. Oligomycin and Rotenone were shown to augment the cell killing of melanoma cells when combined with a high dose rate (2,400 mu/min) compared to untreated cells. Likewise, both melanoma cells and HEM treated with Oligomycin and Rotenone showed significantly lower survival rates at higher doses 2 Gy, 4 Gy and 8 Gy for dose rates 2,400 mu/min and 400 mu/min when compared to untreated cells. Without being limited by theory, it is believed that these results reflect the importance of mitochondrial inhibition as a drug target in melanoma therapy.

Example 2: Mitotracker Assay

It is well-known that melanoma cells up-regulate mitochondrial respiration to partly overcome the damage caused by radiation treatment (Rafehi, H et al., "Clonogenic assay: adherent cells." J. Vis. Exp. 2011 Mar. 13;(49). pii: 2573. doi: 10.3791/2573). In this study, Mitotracker® Red was used to determine mitochondrial activity in irradiated melanoma cells and HEM. Mitotracker® Red is a cell permeant mitochondrial probe that diffuses through the plasma membrane of active mitochondria and is retained there even after fixation of cells. That is, mitochondrial activity is a direct measure of the amount of fluorescent Mitotracker® Red accumulated within the mitochondria.

A Mitotracker® Red CMXRos (Invitrogen, Carlsbad, Calif., Catalog #M7512 or equivalent) assay was performed according to manufacturer's instructions. Briefly, cells were maintained and irradiated as described in Example 1.

Mitotracker® Red stock solution was prepared in dimethyl sulfoxide (DMSO) (Sigma-Aldrich, St. Louis, Mo., Catalog #C6134 or equivalent), aliquoted and stored at −30° C. Stock solution was diluted with appropriate culture media prior to the assay. Cells were treated with 200 µM Mitotracker® Red working solution and incubated for 15 minutes in a humidified incubator (37° C., 5% $CO_2$). Solution was removed and cells were washed with 1×PBS followed by fixing with 2% paraformaldehyde (PFA) (Sigma-Aldrich, St. Louis, Mo., Catalog #P6148 or equivalent) for 30 minutes at room temperature in the dark. Cells were washed with 1×PBS and mounted using DAPI (Sigma-Aldrich, St. Louis, Mo., Catalog #F6057 or equivalent) and fluorescent images immediately were taken with a fluorescent microscope.

Figure 2A:
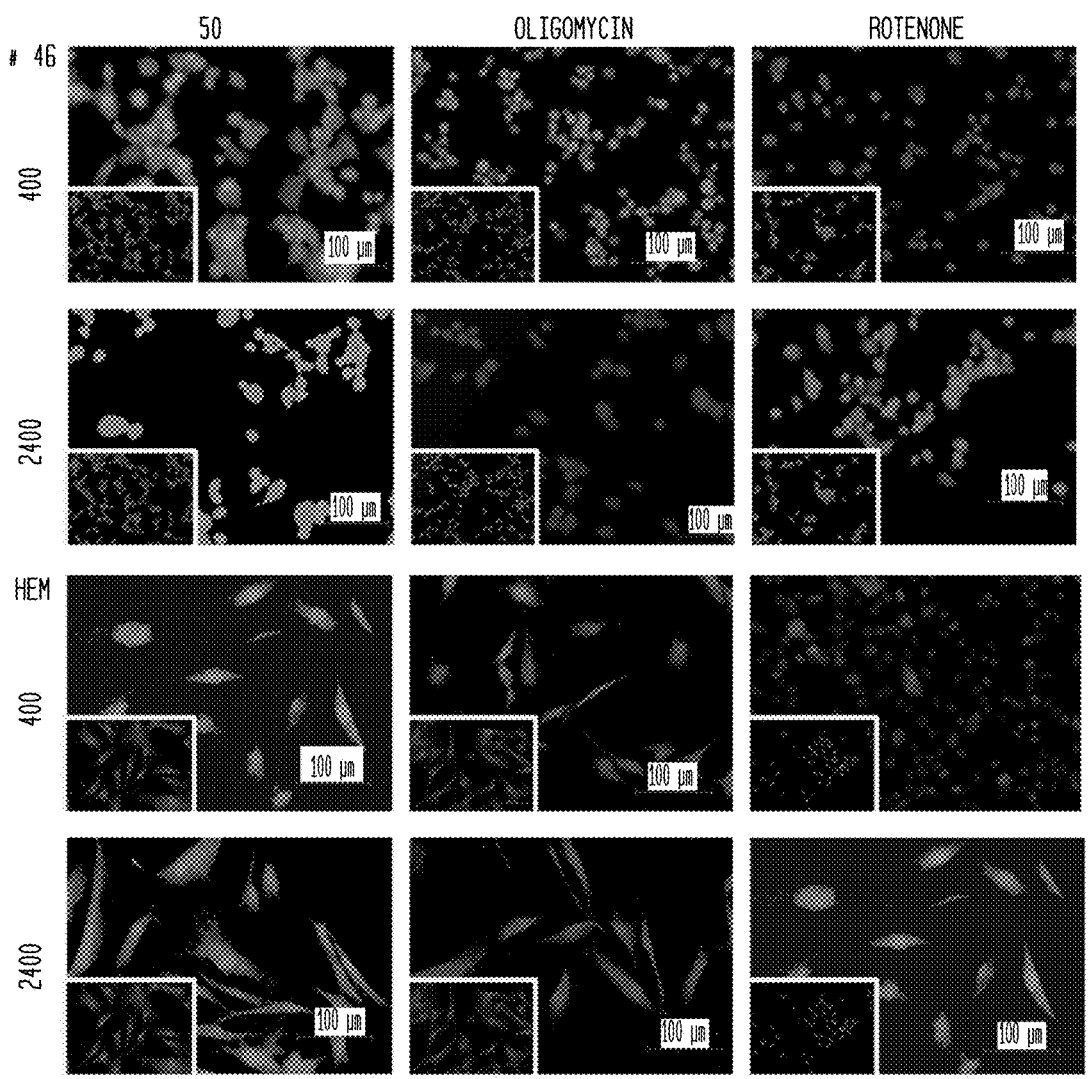
FIG. 2A is a series of images of a mitotracker assay of two types of cells that have been subjected to radiation at two different rates and selectively treated with different mitochondrial inhibitors.

FIG. 2A shows the results of this study. In general, irradiated melanoma cells expressed higher fluorescence than non-irradiated control (Dose 0). Fluorescence was higher in melanoma cells irradiated at 2,400 mu/min compared to 400 mu/min. When mitochondrial respiration was blocked with Oligomycin and Rotenone, mitochondrial activity was reduced below basal levels (Dose 0). Mitochondrial activity in irradiated HEM was not significantly increased over basal levels (Dose 0).

Example 3: Cell Proliferation Assay

An MTT (tetrazolium dye) assay was performed to measure cell proliferation in irradiated melanoma cells and HEM. The MTT assay is based on the ability of metabolically active cells to reduce yellow tetrazolium salt (MTT) to insoluble purple formazan crystals. The formazan crystals are solubized in detergent and quantified by colorimetric analysis. An increase in the formation of formazan crystals (i.e., color) when compared to control cells is indicative of cell proliferation. Conversely, a decrease in the formation of formazan crystals (i.e., color) when compared to control cells is indicative of a reduction in cell viability (e.g., apoptosis or necrosis).

Cells were maintained and irradiated as described in Example 1. A CellTiter 96® $AQ_{ueous}$ One Solution Cell Proliferation Assay (Promega, Madison, Wis., Catalog #G3580 or equivalent) was performed according to manufacturer's instructions. Briefly, a 96-well assay plate (Corning Costar, Tewksbury, Mass., Catalog #CLS3595 or equivalent) containing cells in 100 µL of appropriate culture medium was prepared. Next, 20 µL of $AQ_{ueous}$ One Solution was added to each well of the 96-well plate and the plate was incubated at 37° C. for 1-4 hours in a humidified $CO_2$ incubator. After incubation, 25 µL of 10% sodium dodecyl sulfate (SDS) (Sigma-Aldrich, St. Louis, Mo., Catalog #L3771 or equivalent) was added to each well of the 96-well plate and the plate was read on a microtiter plate reader (Molecular Devices, Sunnyvale, Calif. or equivalent) at an absorbance of 490 nm.

The results of this study are shown in FIG. 2B. Seven (7) days post-irradiation, the cell survival (%) for melanoma cells at dose rate 2,400 mu/min was significantly lower (P value>0.005) than at dose rate 400 mu/min. Treatment of melanoma cells with the mitochondrial inhibitors Oligomycin and Rotenone further reduced the cell survival (%). HEM showed no significant difference in cell proliferation between dose rates.

Example 4: Cell Migration Assay

A cell migration assay was performed in order to identify which of three (3) melanoma cell lines was highly aggressive (i.e., higher migration ability). Human epidermal melanocytes (HEM) were used as a negative control.

The cell migration assay was performed using a QCM™ 24-well Collagen Based Cell Invasion Assay Kit (Chemicon International, Billerica, Mass., Catalog #ECM554) as per manufacturer's instructions. Briefly, melanoma cell lines WC00046, WC00060 and WC00081 (purchased from Coriell Institute of Camden, N.J.) were passaged 2-3 at 80% confluence in RPMI media (Invitrogen, Carlsbad, Calif., Catalog #11875119 or equivalent) with 10% fetal bovine serum (FBS; ATCC Catalog #30-2020 or equivalent), 1% Penicillin/Streptomycin (GIBCO, Carlasbad, Calif., Catalog #15140 or equivalent). HEM were passaged 2-3 at 80% confluence in Mel-M media (ScienCell Research Laboratories, Carlsbad, Calif., Catalog #2201). Cells were starved were by incubating 18-24 hours prior to assay in appropriate serum-free medium. Cells were washed 2 times with sterile phosphate buffer saline (PBS) (Sigma Aldrich, St. Louis, Mo., Catalog No. P5493, or equivalent). Next, 5 mL of Harvesting Buffer per 100 mm dish was added to the cells and the cells were incubated at 37° C. for 5-15 minutes. Cells were then collected and added to 10-20 mL Quenching Medium. Next, cells were pelleted by centrifugation at 1,500 RPM for 5-10 minutes at room temperature. During centrifugation, migration assay plates and reagents were brought to room temperature. After centrifugation, the cell pellets were resuspended in 1-5 mL Quenching Medium, counted and resuspended to $0.5$-$1.0 \times 10^6$ cells/mL. Next, 300 µL of prewarmed serum-free media was added to the interior of the inserts and the ECM layer was allowed to rehydrate for 15-30 minutes at room temperature. After rehydration, 250 µL of media was removed from the inserts without disturbing the membrane. Next, a cell suspension containing $0.5$-$1.0 \times 10^6$ cells/mL in chemo-attractant-free media was prepared and 250 µL of the cell suspension was added to each insert. 500 µL of serum-free media in the presence or absence of chemo-attractant (e.g., 10% FBS) was added to the lower chamber. The plate was covered and incubated for 24-72 hours at 37° C. in a $CO_2$ incubator. Following incubation, cells/media were removed from the top side of the insert by pipetting, the invasion chamber insert was placed into a clean well containing 225 µL of prewarmed Cell Detachment Solution and the plate was incubated for 30 minutes at 37° C. Cells were dislodged from the underside by gently tilting the invasion chamber plate back and forth several times during incubation and the insert was removed from the well. Next, CyQuant GR Dye was diluted 1:75 with 4× Lysis Buffer and 75 µL was added to each well containing 225 µL cell detachment solution with the cells that invaded through the ECMatrix™-coated membrane and incubated for 15 minutes at room temperature. After incubation, 200 µL of the mixture was transferred to a 96-well plate suitable for fluorescence measurement. The plate was read using a Beckman-Coulter plate reader with a 480/520 nm filter set.

Figure 3A:
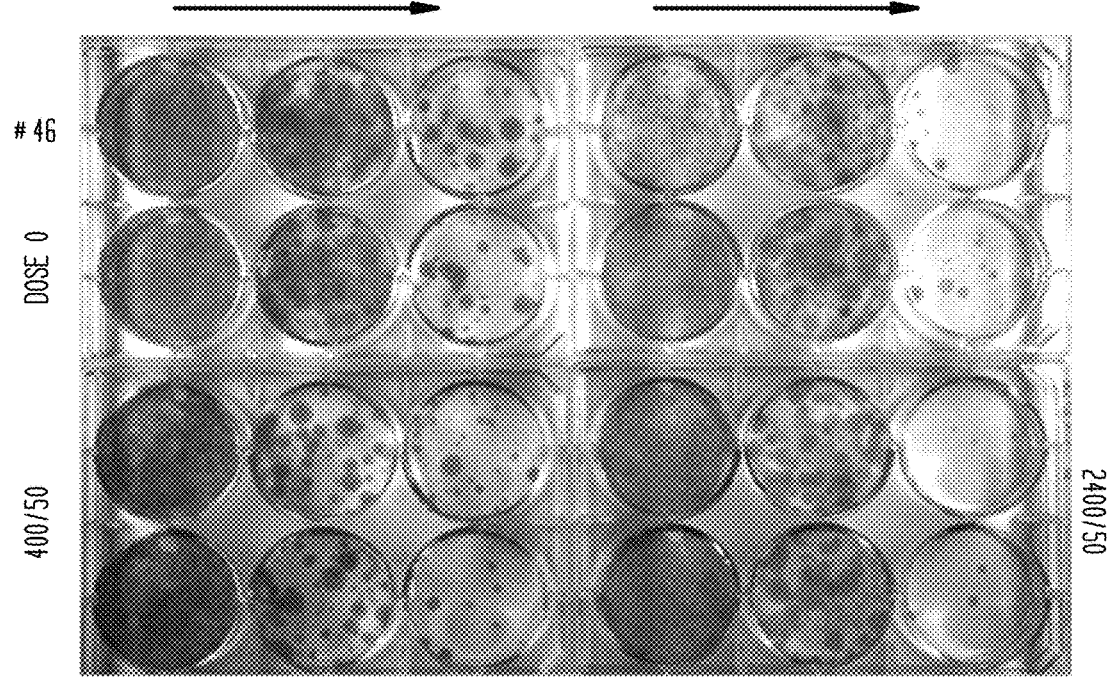
FIG. 3A is an image of a colony assay for cells treated with different doses and rates of radiation.
Figure 3B:
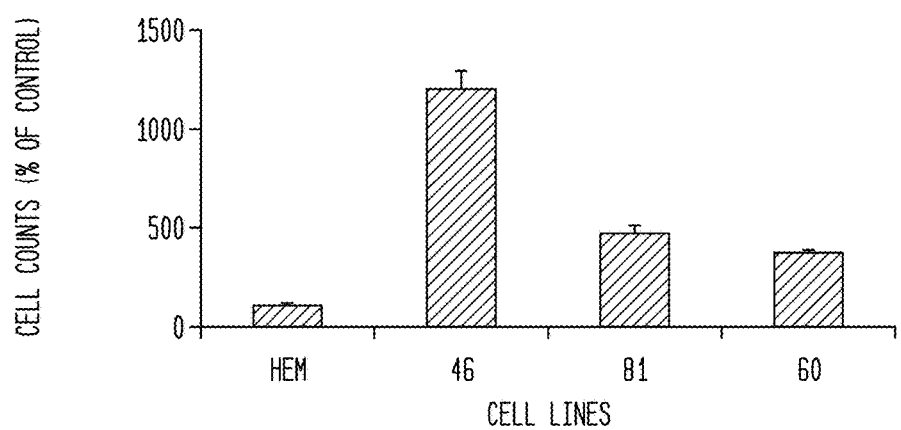
FIG. 3B is a graph of migration assay results for four different types of cells.

The results of the study are shown in FIGS. 3A and 3B. WC00046 (46) was determined to have higher migration abilities than WC00060 and WC00081 when compared to HEM control.

Example 5: Colony Formation Assay

The colony formation assay, or clonogenic assay, is used to determine the ability of a cell to proliferate (i.e., maintain its reproductive ability to form a colony or clone). This assay has been widely used in radiation biology to assess the effects of ionizing radiation on cells (Sadagopan, R. et al., "Characterization and clinical evaluation of a novel IMRT quality assurance system." Journal of Applied Clinical Medical Physics 10.2 (2009)). In this study, three (3) melanoma cell lines were used to compare the effects of different radiation dose rates on cell proliferation. Melanoma cell lines were selected based on their known resistance to radiation therapy. Human epidermal melanocytes (HEM) were used to determine the effect of ionizing radiation on normal cells.

Cells were maintained and irradiated as described in Example 1. Irradiated cells were washed with 1× phosphate buffer saline (PBS) (Sigma Aldrich, St. Louis, Mo., Catalog No. P5493, or equivalent), trypsinized and harvested in 15 mL conical tubes (BD-Falcon, Franklin Lakes, N.J., Catalog #352095 or equivalent). The cells were serially diluted (1:100, 1:1000, 1:10000) and plated in Petri-dishes (BD-Falcon, Franklin Lakes, N.J., Catalog #351007 or equivalent) with the appropriate complete media and allowed to grow colonies for 7-21 days. Colonies were stained with hematoxylin (Sigma-Aldrich, St. Louis, Mo., Catalog #H9627 or equivalent) for 30 minutes after fixing the cells in 100% ethanol (VWR, Radnor, Pa., Catalog #71006-012 or equivalent) for about 20-30 minutes. Petridishes with stained colonies were washed in water, dried overnight and colony counts were recorded.

Figure 4A:
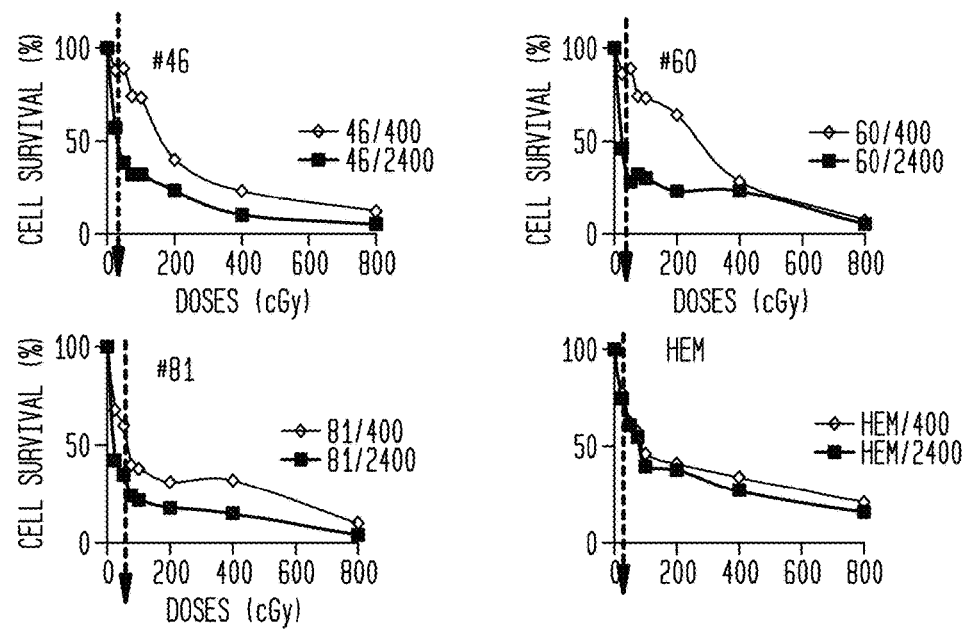
FIG. 4A is a series of comparative graphs of cell survival percentage vs. radiation dose and rate for four different types of cells.
Figure 4B:
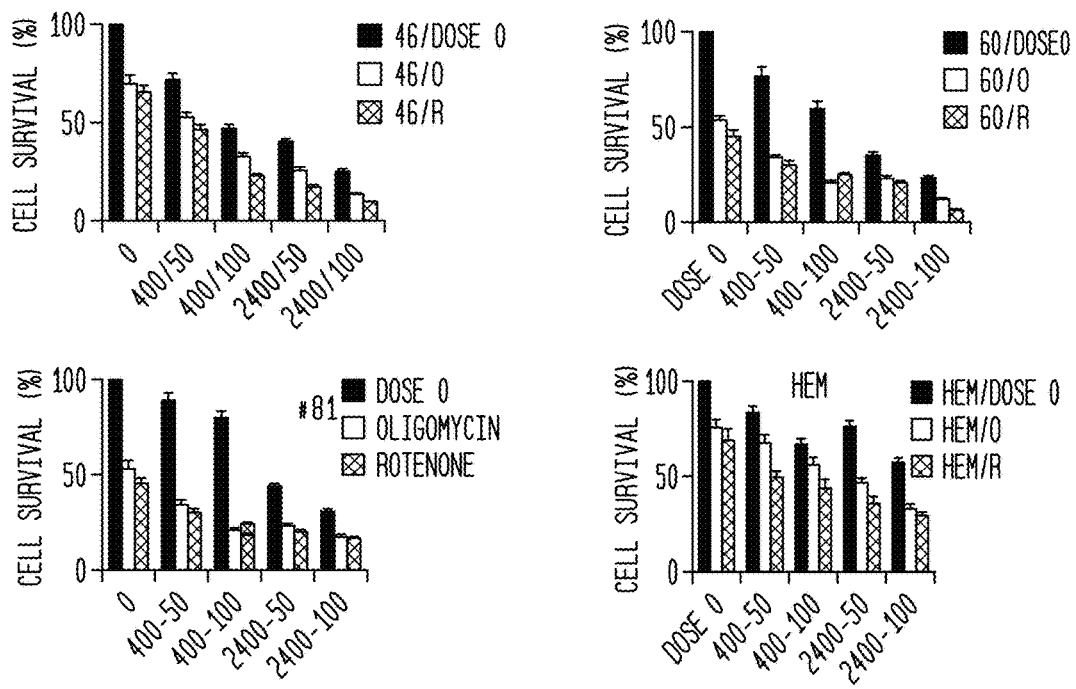
FIG. 4B is a series of comparative graphs of cell survival percentage vs. radiation dose and rate and the presence/absence of mitochondrial inhibitors for four different types of cells.

The results of this study are shown in FIGS. 4A and 4B.

FIG. 4A shows the cell survival (%) of melanoma cells and HEM after exposure to ionizing radiation at 400 mu/min and 2,400 mu/min, for a low total dose of 0.5 Gy. Cell survival (%) for WC00046 was reduced to 38% at 2,400 mu/min compared to 89% at 400 mu/min. Similarly, cell survival (%) for WC00060 was reduced to 28% at 2,400 mu/min compared to 89% at 400 mu/min. Cell survival (%) for WC00081 was reduced to 35% at 2,400 mu/min compared to 60% at 400 mu/min. HEM survival fractions were greater than 60% at both dose rates.

FIG. 4B shows the colony survival fractions of cells treated with the mitochondrial inhibitors Oligomycin and Rotenone. The cell survival (%) for melanoma cells WC00046, WC00060 and WC00081 was further reduced (for example, cell survival (%) for WC00046 was reduced to 25%) at 2,400 mu/min. HEM treated with Oligomycin and Rotenone retained viability and proliferation.

Example 6: RNA Isolation and Quantitative Real-Time PCR

In this study, Quantitative Real-Time PCR (qRT-PCR) was used to measure the change in expression levels of select anti-apoptotic genes, apoptotic genes, mitochondrial respiratory genes, DNA repair and proliferation genes and proto-oncogenes in irradiated melanoma cells and HEM. A list of the genes examined is provided in FIG. 11(A-C).

Cells were maintained and irradiated as described in Example 1. RNA was isolated from the cells using TRIzol® reagent (Invitrogen, Carlsbad, Calif., Catalog #15596-026 or equivalent). Selected genes were amplified by qRT-PCR using the primer sequences provided in Table 1 and detected by SYBR green incorporation. Quantitative Real-Time PCR was performed on the FAST Model 7900HT thermocycler (Applied Biosystems, Foster City, Calif.) to determine relative mRNA expression levels of selected genes. Each 20 μL reaction volume contained 30 ng cDNA template, 10 μL 2× Power SYBR Master Mix (Applied Biosystems, Foster City, Calif., Catalog #4367659 or equivalent), 1 μL 10 μM forward primer, 1 μL, 10 μM reverse primer. PCR conditions were set in standard mode for Power SYBR qRT-PCR performed on FAST 96-well block using MicroAmp Fast Optical 96-well Reaction Plate with Barcode as per manufacturer's instructions. Specifically, PCR conditions were as follows: denaturation at 95° C. for 10 minutes; followed by 40 cycles at: 95° C. for 15 seconds; 60° C. for 1 minute; and a dissociation stage comprised of 1 cycle at 95° C. for 15 seconds; 60° C. for 15 seconds; and 95° C. for 15 seconds. Using GAPDH and B2M as endogenous reference genes, qRT-PCR data were analyzed using SDS 7900HT software v2.2.2 to determine the comparative threshold cycle (Ct) method $2^{-\Delta\Delta Ct}$). Fold change and standard deviation were calculated and represented by bar graphs (data not shown).

TABLE 1

| qRT-PCR primer sequences PRIMER SEQUENCES | |
|---|---|
| NOXA f | gctcaggaacctgactgcat |
| NOXA r | ccatcttccgtttccaagg |
| Mcl-1 f | ttgctggagtaggagctggt |
| Mcl-1 r | gctaggttgctagggtgcaa |
| Bcl-2 f | ttccagagacatcagcatgg |
| Bcl-2 r | tgtccctaccaaccagaagg |
| Bbc-3 f | gacgacctcaacgcacagta |
| Bbc-3 r | gcacctaattgggctccatc |
| PERK f | gacctcaagccatccaacat |
| PERK r | ttggtccctacttgtcctgtg |
| ATF 6 f | cacctaaacaaagggggtca |
| ATF 6 r | tcccaaagtgctgggattac |
| Braf f | cttccgaccagcagatgaag |
| Braf r | ggttgatcctccatcaccac |
| NDUFS4 f | attggcacaggaccagactc |
| NDUFS4 r | tcccatcgctctctggtatc |
| SDHC v2 f | ttagcaggcatgctgttttg |
| SDHC v2 r | ttgggaccctgaatgaagac |
| UCRC f | attcgctgttggcaagaaac |
| UCRC r | tttgcagagggctttgaagt |
| COX4l2 f | gagcttggtgctgaggaaag |
| COX4l2 r | ccagcttcccttctccttct |
| ATPAF2 f | catcacacagggtgaaggtg |
| ATPAF2 r | ttgggttgtccaatgatgtg |
| PTEN f | gaatggagggaatgctcaga |
| PTEN r | cgcaaacaacaagcagtgac |
| MSH-2 f | ggtgttttgtgccatgtgag |
| MSH-2 r | ttggttgcagacctgaggat |
| CCND1 f | ctctcattcgggatgattgg |
| CCND1 r | gtgagctggcttcattgaga |
| BAX f | aagctgagcgagtgtctcaa |

TABLE 1-continued qRT-PCR primer sequences
PRIMER SEQUENCES

| | |
|---|---|
| BAX r | cagttgaagttgccgtcaga |
| COX f | cgtggcttgaatgacttcag |
| COX r | ctcaatgtgaccctcagcaa |
| GAPDH f | tcaccagggctgcttttaac |
| GAPDH r | atgacaagcttcccgttctc |
| B2M f | tgtctttcagcaaggactgg |
| B2M r | cctccatgatgctgcttaca |

Results of this study are shown in FIG. 11(A-C). Expression of apoptotic genes AIF, FAS FASL, PARP1, MDM2 and MDM4 was up-regulated in melanoma cells irradiated at the high dose rate (2,400 mu/min). In addition, expression of mitochondrial respiratory pathway genes Ubiquinol-cytochrome c reductase complex (UCRC), NDUFS4, succinate dehydrogenase (SDHC) and ATP synthase mitochondrial F1 complex assembly factor 2 (ATPAF2) also was up-regulated in melanoma cells. Expression of DNA repair and cell proliferation genes MSH2 and CDK2 was up-regulated in irradiated HEM. Without being limited by theory, this data suggests that HEM can overcome the DNA damage caused by irradiation.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A combination therapy method for treating a radiation resistant skin cancer in a subject comprising
   (a) administering to the subject an amount of a chemotherapeutic agent selected from the group consisting of a mitochondrial inhibitor, a mitotic inhibitor, and a combination thereof; and
   (b) delivering to the subject an amount of irradiation at a total dose as measured over one or a plurality of radiation treatments in a 24 hour period not to exceed 1 Gy at a dose rate of 2,400 cGy/min, wherein the irradiation is delivered by a computer-controlled linear accelerator configured to deliver the irradiation to the radiation resistant skin cancer;
   wherein the amount of the chemotherapeutic agent and the amount of irradiation together constitute an amount effective for treating the radiation resistant skin cancer, and wherein the combination therapy is effective to decrease cell survival percentage (%) of the skin cancer while maintaining cell survival percentage (%) of normal cells.

2. The method according to claim 1, wherein the radiation resistant skin cancer is selected from the group consisting of basal carcinoma, squamous carcinoma, and melanoma.

3. The method according to claim 2, wherein the radiation resistant skin cancer is melanoma.

4. The method according to claim 1, wherein the total dose is selected from the group consisting of 0.25 Gy, 0.5 Gy, 0.75 Gy, and 1 Gy.

5. The method according to claim 4, wherein the total dose is 0.5 Gy.

6. The method according to claim 1, wherein the normal cells are epidermal melanocytes.

7. The method according to claim 1, wherein the chemotherapeutic agent is a mitochondrial inhibitor.

8. The method according to claim 7, wherein the mitochondrial inhibitor is Oligomycin.

9. The method according to claim 7, wherein the mitochondrial inhibitor is Rotenone.

10. The method according to claim 1, wherein the chemotherapeutic agent is paclitaxel.

11. A combination therapy method for inducing apoptosis in radiation resistant skin cancer cells comprising
    (a) administering to the subject an amount of a chemotherapeutic agent selected from the group consisting of a mitochondrial inhibitor, a mitotic inhibitor, and a combination thereof; and
    (b) delivering to the subject an amount of irradiation at a total dose as measured over one or a plurality of radiation treatments in a 24 hour period not to exceed 1 Gy at a dose rate of 2,400 cGy/min, wherein the irradiation is delivered by a computer-controlled linear accelerator configured to deliver the irradiation to the radiation resistant skin cancer;
    wherein the amount of the chemotherapeutic agent and the amount of irradiation together constitute an amount effective for treating the radiation resistant skin cancer cells, and wherein the combination therapy is effective to up-regulate gene expression levels of apoptotic genes in the radiation resistant skin cancer cells while maintaining gene expression levels of apoptotic genes in normal cells.

12. The method according to claim 11, wherein the radiation resistant skin cancer cells are selected from the group consisting of basal carcinoma cells, squamous carcinoma cells, and melanoma cells.

13. The method according to claim 12, wherein the radiation resistant skin cancer cells are melanoma cells.

14. The method according to claim 11, wherein the total dose is selected from the group consisting of 0.25 Gy, 0.5 Gy, 0.75 Gy, and 1 Gy.

15. The method according to claim 14, wherein the total dose is 0.5 Gy.

16. The method according to claim 11, wherein the normal cells are epidermal melanocytes.

17. The method according to claim 11, wherein the apoptotic genes are selected from the group consisting of AIF, FAS, FASL, PARP1, MDM2, and MDM4.

18. The method according to claim 11, further comprising the step of measuring the gene expression levels of the apoptotic genes using quantitative reverse transcriptase polymerase chain reaction (q RT-PCR).

19. The method according to claim 11, wherein the chemotherapeutic agent is a mitochondrial inhibitor.

20. The method according to claim 19, wherein the mitochondrial inhibitor is Oligomycin.

21. The method according to claim 19, wherein the mitochondrial inhibitor is Rotenone.

22. The method according to claim 11, wherein the chemotherapeutic agent is paclitaxel.

* * * * *